(12) United States Patent
Hirose

(10) Patent No.: US 7,847,231 B2
(45) Date of Patent: Dec. 7, 2010

(54) IMAGE SENSOR AND ELECTROMAGNETIC RADIATION IMAGING DEVICE

(75) Inventor: Yutaka Hirose, Kyoto (JP)

(73) Assignee: Panasonic Corporation, Osaka (JP)

( * ) Notice: Subject to any disclaimer, the term of this patent is extended or adjusted under 35 U.S.C. 154(b) by 160 days.

(21) Appl. No.: 12/199,057

(22) Filed: Aug. 27, 2008

(65) Prior Publication Data

US 2009/0057536 A1 Mar. 5, 2009

(30) Foreign Application Priority Data

Aug. 28, 2007 (JP) .............................. 2007-221771

(51) Int. Cl.
G01J 1/20 (2006.01)
H01L 27/00 (2006.01)

(52) U.S. Cl. .............................. 250/208.1; 250/370.08; 348/308

(58) Field of Classification Search .............. 250/208.1, 250/370.08; 348/162, 308
See application file for complete search history.

(56) References Cited

U.S. PATENT DOCUMENTS

| | | | |
|---|---|---|---|
| 4,315,159 A | 2/1982 | Niwa et al. | |
| 5,376,782 A * | 12/1994 | Ikeda et al. | 250/208.1 |
| 5,666,574 A | 9/1997 | Ogawa | 396/233 |
| 7,220,959 B2 * | 5/2007 | Nishimura | 250/226 |
| 2002/0005951 A1 * | 1/2002 | Fukasawa | 356/432 |
| 2002/0134918 A1 * | 9/2002 | Miida | 250/214.1 |
| 2005/0072925 A1 * | 4/2005 | Chen et al. | 250/338.2 |
| 2006/0044439 A1 | 3/2006 | Hiyama et al. | |
| 2006/0266928 A1 | 11/2006 | Takiba et al. | |
| 2007/0218580 A1 * | 9/2007 | Hsu et al. | 438/48 |
| 2009/0050943 A1 * | 2/2009 | Mauritzson | 257/292 |
| 2009/0057536 A1 * | 3/2009 | Hirose | 250/208.1 |

FOREIGN PATENT DOCUMENTS

| | | |
|---|---|---|
| JP | 2002-5828 | 1/2002 |
| JP | 2004-20504 | 1/2004 |
| JP | 2005-37213 | 2/2005 |
| JP | 2005-354568 | 12/2005 |

OTHER PUBLICATIONS

English language Abstract of JP 2004-20504, Jan. 22, 2004.
English language Abstract of JP 2005-37213, Feb. 10, 2005.
English language Abstract of JP 2005-354568, Dec. 22, 2005.

(Continued)

Primary Examiner—John R Lee
(74) Attorney, Agent, or Firm—Greenblum & Bernstein, P.L.C.

(57) ABSTRACT

To provide a small-size image sensor and electromagnetic radiation imaging device which can obtain a good image without relying on the condition of an object, the image sensor including a plurality of pixel units arranged two-dimensionally, wherein each of the plurality of pixel units includes: a first photodiode and a second photodiode; a readout circuit which reads a signal generated by the first photodiode and a signal generated by the second photodiode, and outputs the read signals, the readout circuit being connected to the first photodiode and the second photodiode; and a difference circuit which outputs a difference signal corresponding to a difference between the signal read from the first photodiode and the signal read from the second photodiode, the difference circuit being connected to the readout circuit.

16 Claims, 16 Drawing Sheets

OTHER PUBLICATIONS

English language Abstract of JP 2002-5828, Jan. 9, 2002.

Kiyomi Sakai ed., "Terahertz Optoelectronics," Topics in Applied Physics, vol. 97, pp. 331-381 (2005).

B. B. Hu and M. C. Nuss, "Imaging with Terahertz Waves," Optics Letters, vol. 20, No. 16, p. 1716-1718 (Aug. 1995).

F. Miyamaru, T. Yonera, and M. Hangyo, "Terahertz Two-Dimensional Electrooptic Sampling Using High Speed Complementary Metal-Oxide Semiconductor Camera," Japanese Journal of Applied Physics, vol. 43, No. 4A, pp. L489-L491 (Mar. 2004).

A. Yariv, "Optical Electronics," Holt-Saunders International Editions, $3^{rd}$ Ed., pp. 291-294 (1985).

J. Hynecek, "Analysis of the Photosite Reset in FGA Image Sensors," IEEE Transactions Electron Devices, vol. 37, No. 10, pp. 2193-2200 (Oct. 1990).

S.C. Fan, R. Gregorian, G.C. Temes, and M. Zomorrdi, "Switched-Capacitor Filters Using Unit-Gain Buffers," Proc. IEEE Int. Symp. Circuits and Systems, pp. 334-337 (1980).

E. Hecht, "Optics," $4^{th}$ ed., Addison Wesley San Francisco, pp. 425-431 (2002).

* cited by examiner

IMAGE SENSOR AND ELECTROMAGNETIC RADIATION IMAGING DEVICE

BACKGROUND OF THE INVENTION (1) Field of the Invention

The present invention relates to image sensors and devices to which the image sensor is applied and, in particular, to an image sensor and an electromagnetic radiation imaging device which image THz electromagnetic radiation.

(2) Description of the Prior Art

In recent years, the development of THz electromagnetic radiation imaging devices has been advanced for security check, a medical test, a food analysis, a drug analysis, environmental monitoring, and so on (See the following: Non-patent Reference 1: Kiyomi Sakai ed., "Terahertz Optoelectronics", Springer Verlag, 2005, pp. 331-381; Non-patent Reference 2: B. B. Hu and M. C. Nuss, Opt. Lett. Vol. 20, p. 1716, (1995); Patent Reference 1: Japanese Unexamined Patent Application Publication No. 2002-5828; Patent Reference 2: Japanese Unexamined Patent Application Publication No. 2004-20504; and Patent Reference 3: Japanese Unexamined Patent Application Publication No. 2005-37213).

In these techniques, electromagnetic radiation has a frequency band between 0.1 THz and 100 THz in a region (hereinafter, referred to as THz electromagnetic radiation), and the THz electromagnetic radiation is generated by a THz electromagnetic radiation source. An object to be inspected is irradiated with the THz electromagnetic radiation. Accordingly, the THz electromagnet radiation has spatial distribution information of a physical property (shape, material, and so forth) of the object as an amount of modulation of the intensity of reflected wave or transmitted wave or of phase-space distribution. The spatial distribution information of the physical property of the object is composed as a two-dimensional image by receiving the amount of the THz electromagnetic radiation.

For a method of obtaining two-dimensional information of the object to be inspected, as initially described in Non-patent Reference 2, a method is adopted in which a beam of THz electromagnetic radiation is focused on a portion of the object through a lens, the object is scanned with the beam of THz electromagnetic radiation, modulated THz electromagnetic radiation is successively received by a receiver which is capable of receiving only one-dimensional information, and two-dimensional information is formed.

This method, however, needs many hours, a long time period, to collect all data of the two-dimensional information, and is unpractical for an inspection device for which it is necessary to complete an inspection in a real time.

As a way of covering the shortcoming, the THz electromagnetic radiation imaging device shown in FIG. 1 has been reported in Non-patent Reference 3: F. Miyamaru, T. Yonera, M. Tani and M. Hangyo, Japanese Journal of Applied Physics, Vol. 43, p. L489-L491, (2004).

In FIG. 1, an ultrashort pulsed light source 1601 generates ultrashort pulsed light with 100 fs pulse width at a frequency of 1 kHz, and a polarization beam splitter 1602 splits the ultrashort pulsed light into p-polarized light as pump light 1603 and s-polarized light as probe light 1604.

The pump light 1603 enters, via an optical delay line 1605, a THz electromagnetic radiation emitter 1606 which is structured with a photoconductive switch having an electrode pair formed on a semi-insulating GaAs wafer at an interval of 10 mm, and THz electromagnetic radiation 1607 is generated. The THz electromagnetic radiation 1607 generated in this manner is a beam having a wide beam width and extremely high collimating property, and is radiated to an object to be inspected 1608 having two-dimensional transmission distribution in a plane perpendicular to a traveling direction of the THz electromagnetic radiation 1607.

The THz electromagnetic radiation 1607 that penetrated the object to be inspected 1608 becomes a spatially intensity-modulated beam with two-dimensional transmission characteristics of the object to be inspected 1608. The beam forms an image in an electric field modulator 1613 which is in a subsequent stage and which is made of a ZnTe crystal using a polyethylene lens 1609.

After a probe light course altering mirror 1610 alters a course of the probe light 1604 and further a beam expander 1611 expands a beam width of the probe light 1604, the probe light 1604 enters a silicon mirror 1612 having silicon wafers and shares an optical axis with the intensity-modulated THz electromagnetic radiation 1607 that transmitted through the silicon mirror 1612. In other words, the probe light 1604 and the THz electromagnetic radiation 1607 are superimposed.

The superimposed probe light 1604 and THz electromagnetic radiation 1607 enter the electric field modulator 1613 made of a ZnTe crystal whose [110] plane is disposed perpendicular to the optical axis.

In a subsequent stage of the electric field modulator 1613, a phase plate 1614, a polarization plate 1615, and a two-dimensional CMOS image sensor 1616 are arranged in this order, the polarization plate 1615 transmitting only linear polarized light having a polarization plane perpendicular to the probe light 1604, the two-dimensional CMOS image sensor 1616 having one photodiode per one pixel receiving transmitted light from the polarized plate 1615.

In order to maximize a signal-to-noise ratio (S/N ratio) of an image to be obtained while keeping an amount of transmitted light of the polarization plate 1615 minimum, in the case where the THz electromagnetic radiation 1607 does not enter the electric field modulator 1613 simultaneously with each pulse of the probe light 1604, that is, in the case where a THz electromagnetic radiation pulse and a probe pulse are asynchronous, the phase plate 1614 sets, in its subsequent stage, the polarization plane of the probe light 1604 to make deflection angles of approximately 2° to 3° from a direction perpendicular to a transmission polarization plane of the polarization plate 1615.

Suppression of an amount of light transmitted through a polarization plate by using the probe light 1604 in a linear polarized wave and by controlling a polarization plane of the probe light 1604 is hereinafter referred to as suppression of a phase bias of the probe light 1604.

In the case where both of the above-mentioned pulses are not synchronized, the probe light 1604 whose amount of light is suppressed, that is, transmitted light corresponding to a minimal amount of bias from the polarization plate enters the CMOS image sensor 1616. In the case where, however, the THz electromagnetic radiation pulse and the probe light pulse enter the electric field modulator 1613 simultaneously, that is, in the case where both of the pulses are synchronized, a polarization state of the probe light after transmitting through the electric field modulator 1613 is that deflection angles are further rotated approximately by 0.02° in comparison to a case where the probe light pulse is asynchronous with the THz electromagnetic radiation pulse. As a result, an approximately one percent amount of intensity modulation can be expected.

In the THz electromagnetic radiation imaging device, two successive probe light pulses have information modulated by the THz electromagnetic radiation and unmodulated information, and information of two successive images formed by the two successive probe light pulses is obtained by synchronizing a pulse period of the probe light and a pulse period of a laser light source in a synchronization circuit 1617. An image captured earlier in time is temporary stored, and an image processing circuit 1618 calculates a difference between the images in a period when a next image signal is outputted. Accordingly, an image of transmission characteristics of the object to be inspected 1608 can be obtained, the image being formed by the THz electromagnetic radiation.

SUMMARY OF THE INVENTION

The following problems, however, arise with the above-mentioned techniques.

In other words, since the THz electromagnetic radiation device uses only a unidirectional polarization component as a signal by one polarization plate as mentioned above, it is necessary to obtain, at different times, image data at a time when the probe light is unmodulated by the THz electromagnetic radiation and image data at a time when the probe light is modulated by the THz electromagnetic radiation and to output a difference between images. With this method, in comparison to time necessary for obtaining two images such as still pictures, concerning an object moving within a sufficiently long time, it is possible to reproduce an actual object. Concerning the object moving and performing in a short time equal to or less than image acquisition time, however, image distortion, out-of-focus image and the like occur, and a good image cannot be obtained. In addition, since a circuit which temporally stores data of one frame image obtained prior to obtaining two images at different times becomes necessary, the THz electromagnetic radiation imaging device grows in size.

Furthermore, with the conventional techniques, in order to suppress intensity of light entering an image sensor at a time of unmodulation as much as possible and to avoid an excess input of light signal to a pixel of the image sensor, the probe light at the time of unmodulation is linear polarized light in a polarization state and the probe light modulated by the THz electromagnetic radiation is an elliptical polarized light in a polarization state. In this case, however, these phase bias points cannot maximize a signal-to-noise ratio (S/N ratio) of an image to be obtained by an electric field modulation system. In order to maximize the signal-to-noise ratio (S/N ratio) to be obtained, it is desirable that probe light entering a polarized light filter is ideally circular polarized light at the time of unmodulation and has an equal amount of polarization components perpendicular to each other (See Non-patent Reference 4: Yariv, A. (co-translated by Tada and Kamiya) "Introduction to Optical Electronics", Maruzen, pp. 245, (1974)). To realize this system, it is necessary to divide the probe light into two types of the probe light with equal intensity, to transmit each type of the probe light through two types of polarization plates perpendicular to each other, to arrange an independent image sensor in each subsequent stage of the polarization plates, and to get a difference between two images obtained by both of the image sensors. Consequently, plural image sensors are necessary, and the THz electromagnetic radiation imaging device becomes complex.

Further, with the conventional techniques, to improve the S/N ratio in the case of a low signal level, it is necessary to obtain and accumulate plural image planes and a huge external memory and a long image obtainment time become necessary, which are impractical.

The present invention has been conceived to solve the above-mentioned problems, and the first purpose of the present invention is to provide a small image sensor and an electromagnetic radiation imaging device which can obtain a good image without relaying on the condition of an object.

Furthermore, the second purpose of the present invention is to provide the image sensor and the electromagnetic radiation imaging device which can detect an amount of modulation of modulated probe light without controlling the phase bias of probe light and saturating a circuit.

Moreover, the third purpose of the present invention is to provide the image sensor and the electromagnetic radiation imaging device which can improve an S/N ratio even in the case where a signal level is low.

In order to solve the above-mentioned problems, the image sensor according to the present invention is an image sensor including a plurality of pixel units arranged two-dimensionally, wherein each of the plurality of pixel units includes: a first photodiode and a second photodiode; a readout circuit which reads a signal generated by the first photodiode and a signal generated by the second photodiode, and outputs the read signals, the readout circuit being connected to the first photodiode and the second photodiode; and a difference circuit which outputs a difference signal corresponding to a difference between the signal read from the first photodiode and the signal read from the second photodiode, the difference circuit being connected to the readout circuit. Here, the image sensor may further include: a first polarized light filter above the first photodiode; and a second polarized light filter above the second photodiode, wherein the first polarized light filter and the second polarized light filter each have different polarized light transmission characteristics. In addition, the image sensor may further include: a first wavelength filter above the first photodiode; and a second wavelength filter above the second photodiode, wherein the first wavelength filter and the second wavelength filter each have different wavelength transmission characteristics.

With this structure, in the case where the image sensor is used for detecting an amount of modulation of probe light modulated with respect to a direction of polarization plane and a wavelength, a filter is arranged above the first photodiode and the second photodiode, respectively, and an amount of probe light entering each photodiode is set to be equal in a predetermined reference state, for example, when the amount of modulation of probe light is 0, that is, when the probe light is not modulated.

For instance, an output is deterred by entering probe light which becomes circular polarized light when unmodulated into two photodiodes and by generating equal amount of charge at the first photodiodes and the second photodiodes respectively. When the probe light is modulated, a difference in an amount of received light according to the amount of modulation generated by difference in filter characteristics is generated for each photodiode, and it becomes possible to detect a difference signal according to a difference in an amount of accumulated charge. Accordingly, in the case where the unmodulated light enters into the two photodiodes, current generated at the two photodiodes does not affect a signal, and it becomes possible to detect a signal resulting from the modulated light only in the case where the modulated light enters into the two photodiodes.

This allows the difference between the signals of the two photodiodes to be outputted within a period for accumulating signal for one frame image. Accordingly, it is not necessary to obtain, at different times, image data when the probe light is unmodulated and image data when the probe light is modulated. In addition, a circuit, such as an external memory, which temporally stores data for one frame image obtained prior to obtaining the two images at different times, is not necessary. As a result, it is possible to obtain a small-sized image sensor which can obtain a good image without relying on the condition of an object. Furthermore, it is possible to obtain an image sensor which can output an image at high speed.

Moreover, it is possible to obtain an image sensor which can detect the amount of modulation of modulated probe light without suppressing a phase bias of the probe light and accompanying decrease in an amount of signal.

Furthermore, since a difference operation is performed in parallel for all of the pixel units and a difference signal is outputted in parallel, it is possible to obtain an image sensor which can perform an output operation at higher speed.

Moreover, the pixel unit may further include an integration circuit which integrates the difference signal and outputs the integrated difference signal as a pixel signal.

Since, with this structure, a minute difference signal can be repeatedly read, the difference signal can be integrated by the integration circuit, and a noise component can be reduced, an S/N ratio can be improved even in the case where a signal level is low.

Furthermore, the integration circuit may include an operational amplifier and a feedback capacitor, the operational amplifier having one input terminal connected to an output of the difference circuit and the other input terminal connected to constant potential, and the feedback capacitor being inserted between the one input terminal and an output terminal of the operational amplifier.

With this structure, it becomes possible to integrate the minute difference signal in the feedback capacitor and to improve the S/N ratio.

Moreover, the readout circuit may simultaneously output the signal generated by the first photodiode and the signal generated by the second photodiode, and the difference circuit may include a first capacitor having one terminal connected to the first photodiode and the other terminal connected to the second photodiode.

With this structure, it becomes possible to perform the difference operation not with the commonly used difference circuit including plural transistors but with the least number of circuit elements. As a result, it is possible to obtain the small-sized image sensor.

Furthermore, the integration circuit may include a first transistor and a second capacitor, the first transistor being included in a source follower circuit having a constant current load, and the second capacitor being inserted between a gate of the first transistor and constant potential, and, in the integration circuit, the difference signal may be inputted as a gate-to-source voltage of the first transistor.

With this structure, it becomes possible to perform the difference operation not with the commonly used difference circuit including plural transistors but with the least number of circuit elements. Especially, in the case where a source follower is with a constant current load, a proportional relationship between an input signal and an output signal of the integration circuit is maintained and quantitative signal operation becomes possible. Simultaneously, saturation of signal level in a nonlinear operation at the time of integration is suppressed, and it becomes possible to realize a high S/N ratio and a dynamic range.

Moreover, the integration circuit may include a second transistor having a source which is grounded and a third capacitor inserted between a gate and a drain of the second transistor, and, in the integration circuit, the difference signal may be inputted as a gate-to-source voltage of the second transistor.

With this structure, it becomes possible to perform the integration operation not using an operational amplifier which needs plural transistors but with the less number of transistors.

Furthermore, readout circuit may sequentially output the signal generated by the first photodiode and the signal generated by the second photodiode, and the difference circuit may include a correlated double sampling circuit having a fourth capacitor which accumulates a difference signal corresponding to a difference between the signals sequentially outputted by the readout circuit.

Since, with this structure, the signal from the first photodiode and the signal from the second photodiode share a common noise component, it becomes possible to calculate the difference between the signal of the first photodiode and the signal of the second photodiode, the calculation resulting in calculation of a difference between a reset signal and a photodiode signal which is necessary in outputting a signal component of a normal photodiode. Further, it becomes possible to obtain, with the less number of elements, the difference between the signal of the first photodiode and the signal of the second photodiode. Especially, it is possible to store, in a capacitor in a subsequent stage of two capacitors, the difference signal between the signal of the first photodiode and the signal of the second photodiode and to perform the difference operation with the minimum number of circuit elements by setting connection point voltages of the two series-connected capacitors included in the correlated double sampling circuit to different voltages in a period during which the signal of the first photodiode is inputted to the difference circuit and a period during which the signal of the second photodiode is inputted to the difference circuit.

Moreover, a capacitance value of the fourth capacitor may be larger than a capacitance value of the second capacitor or the third capacitor.

With this structure, when performing the integration operation, it becomes possible to amplify a minute difference signal by an amplification factor proportional to a capacitor ratio of the fourth capacitor and the second capacitor or the third capacitor and to realize a higher S/N ratio.

In addition, the integration circuit may further include a fifth capacitor which is connected in parallel with the fourth capacitor and which is charged at a predetermined voltage.

With this structure, it is possible to supply, using a voltage charged at the fifth capacitor, a bias necessary for the first transistor or the second transistor to operate in a saturated region to the gate of the first transistor or the second transistor, and to surely charge the difference signal between the signal of the first photodiode and the signal of the second photodiode at the second capacitor or the third capacitor.

Furthermore, a clamp voltage of the correlated double sampling circuit may be lower than a threshold voltage of the first transistor or the second transistor.

With this structure, it is possible to realize, with the clamp voltage of the correlated double sampling circuit, a bias function of the integration circuit served by the fifth capacitor. Accordingly, the fifth capacitor becomes unnecessary, and drastic reduction of the number of components and a stable operation of a circuit become possible.

In addition, the pixel signal may be generated within a time of accumulating data for one frame image.

With this structure, it becomes possible to perform the difference and integration operations synchronized with a period for signal output operation of the image sensor and to cause the image sensor to output a signal in real time by incorporating the structure in which a processing speed of the image sensor is increased.

Moreover, an electromagnetic radiation imaging device includes: an electromagnetic radiation source which generates electromagnetic radiation; a light source which generates probe light; a superimposing optical element which superimposes, with the probe light, the electromagnetic radiation that has transmitted through or reflected off an object; an electro-optical modulation element into which the superimposed electromagnetic radiation and probe light enter, and which modulates a specific physical quantity of the probe light according to an electric field of the electromagnetic radiation; and the image sensor which captures the probe light that has been modulated.

With this structure, although the probe light in circular polarization state is entered, it becomes possible to output, in the same frame period, an amount of modulation of the probe light modulated by electromagnetic radiation without controlling a phase bias of the probe light which is not modulated by the electromagnetic radiation and without plural image sensors. Consequently, it is possible to realize a small-sized electromagnetic radiation imaging device which can obtain a good image without relying on the condition of an object. In addition, it is possible to realize the electromagnetic radiation imaging device which can detect an amount of modulation of modulated probe light without controlling the phase bias of probe light and saturating a circuit.

Here, the light source may generate pulsed probe light, and the image sensor may capture the modulated probe light in synchronization with a pulse of the probe light.

With this structure, it becomes possible to perform the difference and integration operations in synchronization with a signal input cycle, to narrow a noise band, and to realize a higher S/N ratio.

Furthermore, the method for driving the image sensor according to the present invention may include: supplying a predetermined voltage of the fifth capacitor to the integration circuit; and inputting a difference signal to the integration circuit after the supplying of the predetermined voltage.

With this structure, it becomes possible to avoid an unstable state caused when the fifth capacitor and the fourth capacitors are simultaneously connected to the second capacitor or the third capacitor, that is, the gate of the first transistor or the second transistor, and the stable operation of the circuit is ensured.

With the image sensor according to the present invention, it is possible to output the difference between the signals of the different photodiodes within a period for accumulating signal for one frame image. In particular, when polarized light filters each of which has a different polarization property and each of which is arranged above each of the photodiodes included in the pair of photodiodes, it becomes possible to output the difference between different polarization components of the incident light within a period for generating one image. Similarly, when the wavelength filters each of which has different transmission characteristics and each of which is arranged above each of the photodiodes included in the pair of photodiodes, it becomes possible to output the difference between different wavelength components of the incident light within the period for generating one image. Further, when the polarization characteristics or the wavelength characteristics of the incident light entering into the image sensor is electro-modulated by the THz electromagnetic radiation, it is possible to realize high speed THz electromagnetic radiation imaging with a high S/N ratio with a simple device.

FURTHER INFORMATION ABOUT TECHNICAL BACKGROUND TO THIS APPLICATION

The disclosure of Japanese Patent Application No. 2007-221771 filed on Aug. 28, 2007 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings which illustrate a specific embodiment of the invention. In the drawings.

DESCRIPTION OF THE PREFERRED EMBODIMENT(S)

Embodiment 1

The following describes an image sensor according to an embodiment 1 of the present invention with reference to FIGS. 2 to 6.

Figure 1:
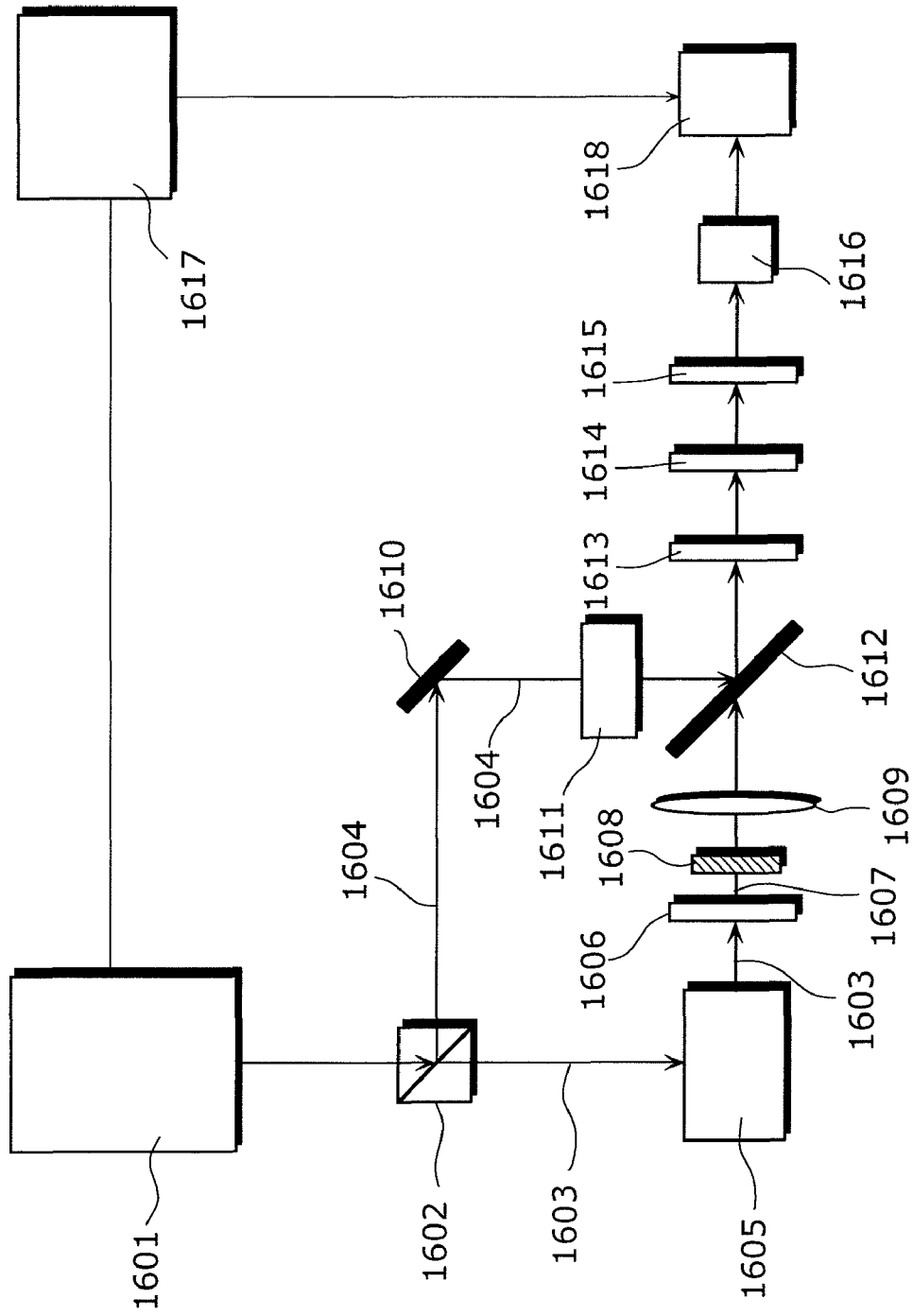
FIG. 1 schematically illustrates a structure of a conventional THz electromagnetic radiation imaging device.
Figure 2:
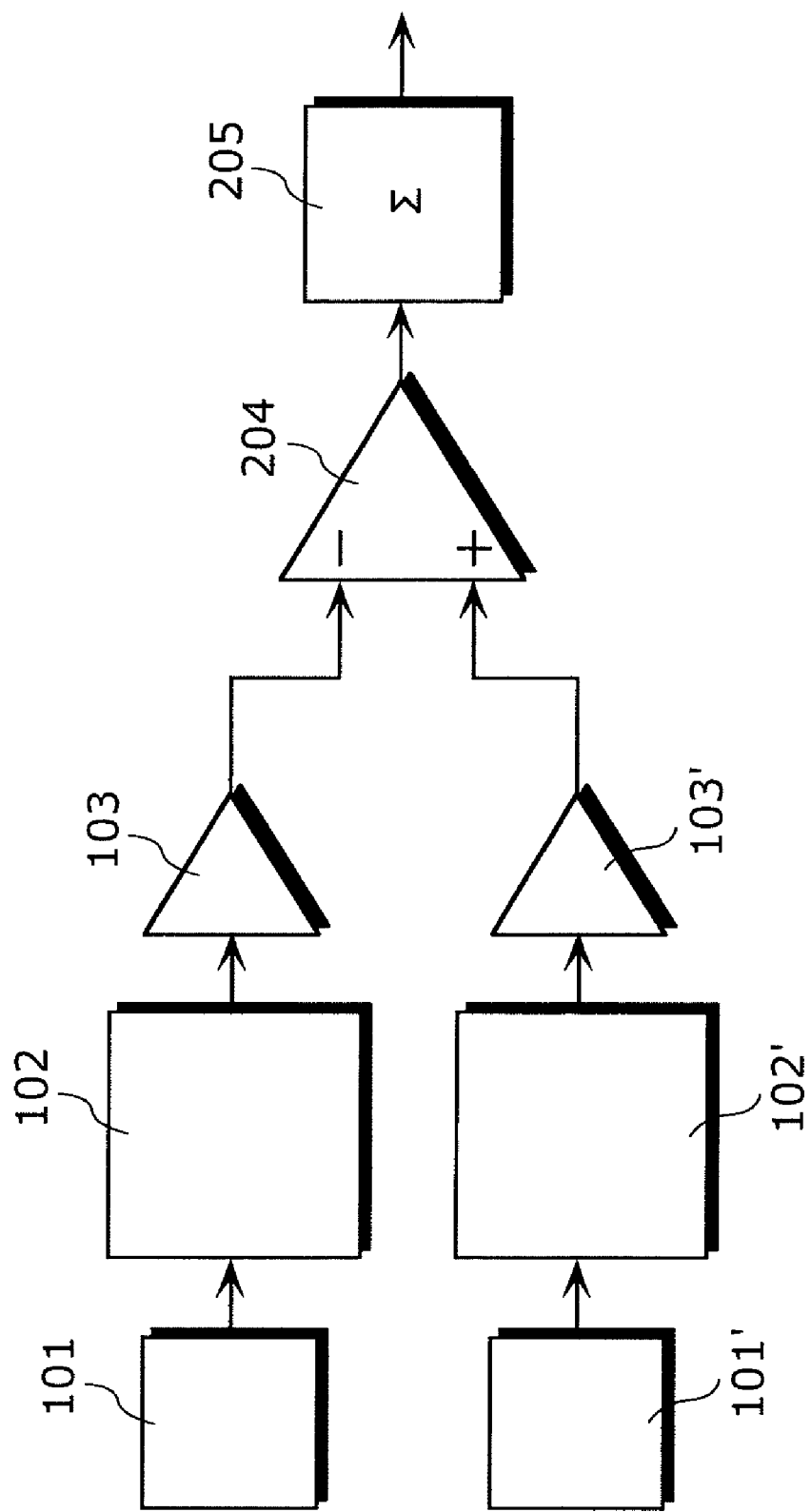
FIG. 2 is a circuit diagram illustrating an operating principle of an image sensor according to an embodiment 1 of the present invention.

FIG. 2 is a circuit diagram illustrating an operating principle of the image sensor according to the embodiment 1.

The circuit includes a pair of adjacent photodiodes 101 and 101', a pair of readout circuits 102 and 102', a pair of signal output circuits 103 and 103', a difference circuit 204, and an integration circuit 205. In the circuit, the respective readout circuits 102 and 102' transfer signal charges accumulated by the photodiodes 101 and 101' to the signal output circuits 103 and 103' in a subsequent stage. Further, a signal output from each of the photodiodes 101 and 101' is inputted to the difference circuit 204 in a subsequent stage, and, for example, a signal showing a difference between different polarization components or different wavelength components (difference signal) is detected. Since a difference output is extremely weak, reading of the same data is repeated. A difference signal at each time of reading is outputted to the integration circuit 205 in the subsequent stage, and the integration circuit 205 accumulates and integrates the difference signal. A random noise component is reduced when performing the integration.

Figure 3:
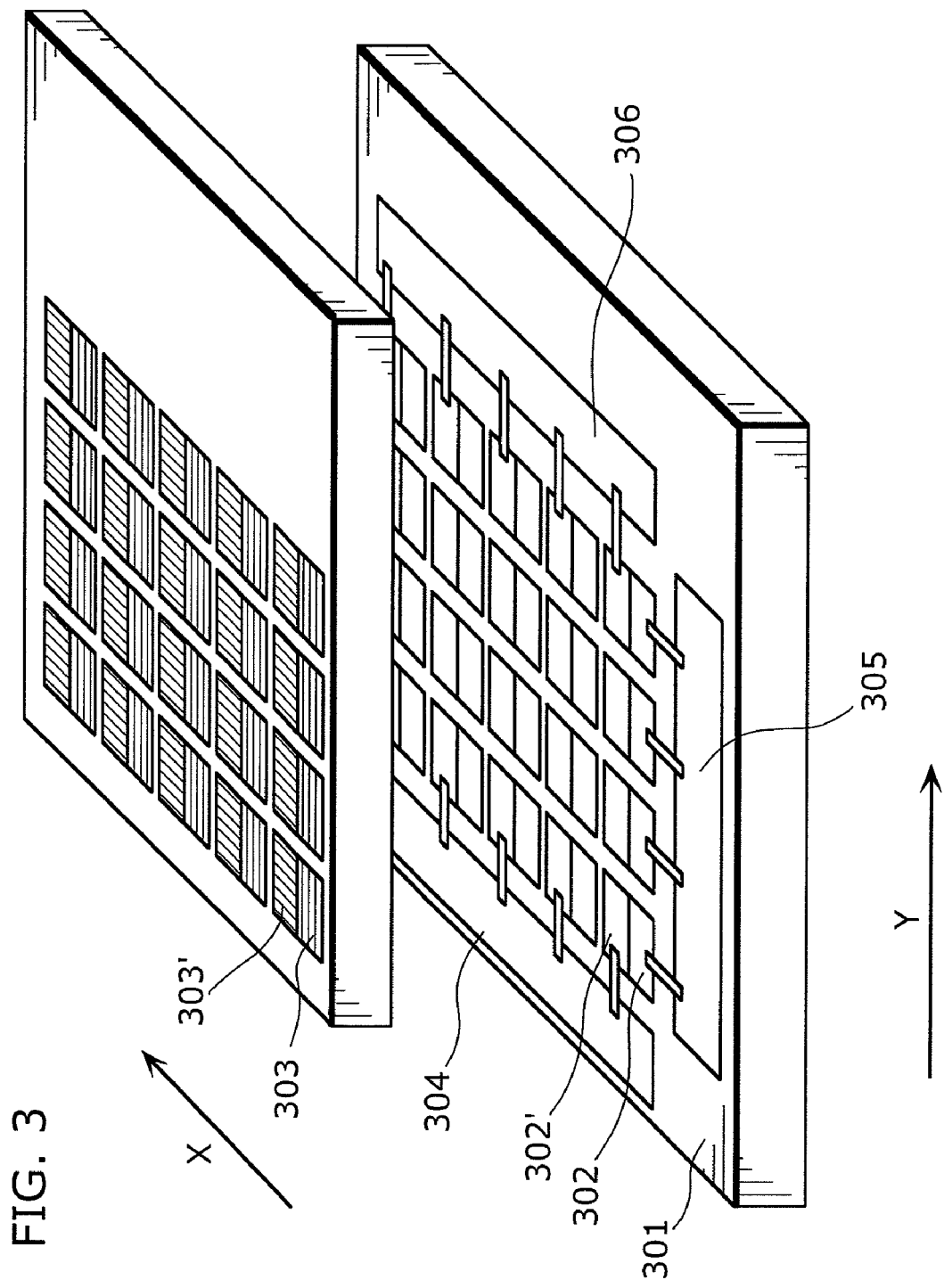
FIG. 3 illustrates a whole structure of the image sensor according to the embodiment 1.

FIG. 3 illustrates a whole structure of the image sensor according to the embodiment 1.

The image sensor includes a Si substrate 301, plural photodiodes 302 and 302', plural polarized light filters 303 and 303', a signal process driving circuit 304, a row scanning circuit 305, and a column scanning circuit 306.

It is to be noted that, in the present invention, the photodiode 302 is an example of a first photodiode, and the photodiode 302' is an example of a second photodiode. Moreover, in the present invention, the polarized light filter 303 is an example of a first polarized light filter, and the polarized light filter 303' is an example of a second polarized light filter.

In the image sensor, two photodiodes in the Si substrate 301, that is, the photodiode 302 and the equivalent photodiode 302' form a pair. Moreover, pairs of photodiodes, each of which is equivalent to the above-mentioned pair of photodiodes, are regularly arranged two-dimensionally in a column direction (X direction) and a row direction (Y direction). A circuit for sequentially reading signal charges generated from incident light at the photodiodes 302 and 302' is arranged around each pair of photodiodes.

The polarized light filters 303 and 303' which pass through only polarized light having a polarization plane in either X direction or Y direction are arranged on each pair of photodiodes. That is to say, the polarized light filter 303 which is made of thin metallic wires in direction perpendicular to Y direction and which passes only Y-direction polarized light is arranged on the photodiode 302, and the polarized light filter 303' which is made of thin metallic wires in direction perpendicular to X direction and which passes only X-direction polarized light is arranged on the photodiode 302'.

The signal process driving circuit 304 distributes, to a pixel including one pair of photodiodes, a driving signal which causes execution of reading a signal from each pair of photodiodes, execution of detecting the difference signal of each pair of photodiodes, and execution of performing integration and arithmetic processing on the difference signal. In the image sensor, the difference signal of each pair of photodiodes on which the integration and arithmetic processing has been performed is read as a pixel signal for one pixel. The row scanning circuit 305 selects a row to be read, the column scanning circuit 306 sequentially outputs, to a horizontal signal output line, the signal of each pair of photodiodes in the selected row on which the integration and arithmetic processing has been performed, and then the pixel signal is read.

Figure 4:
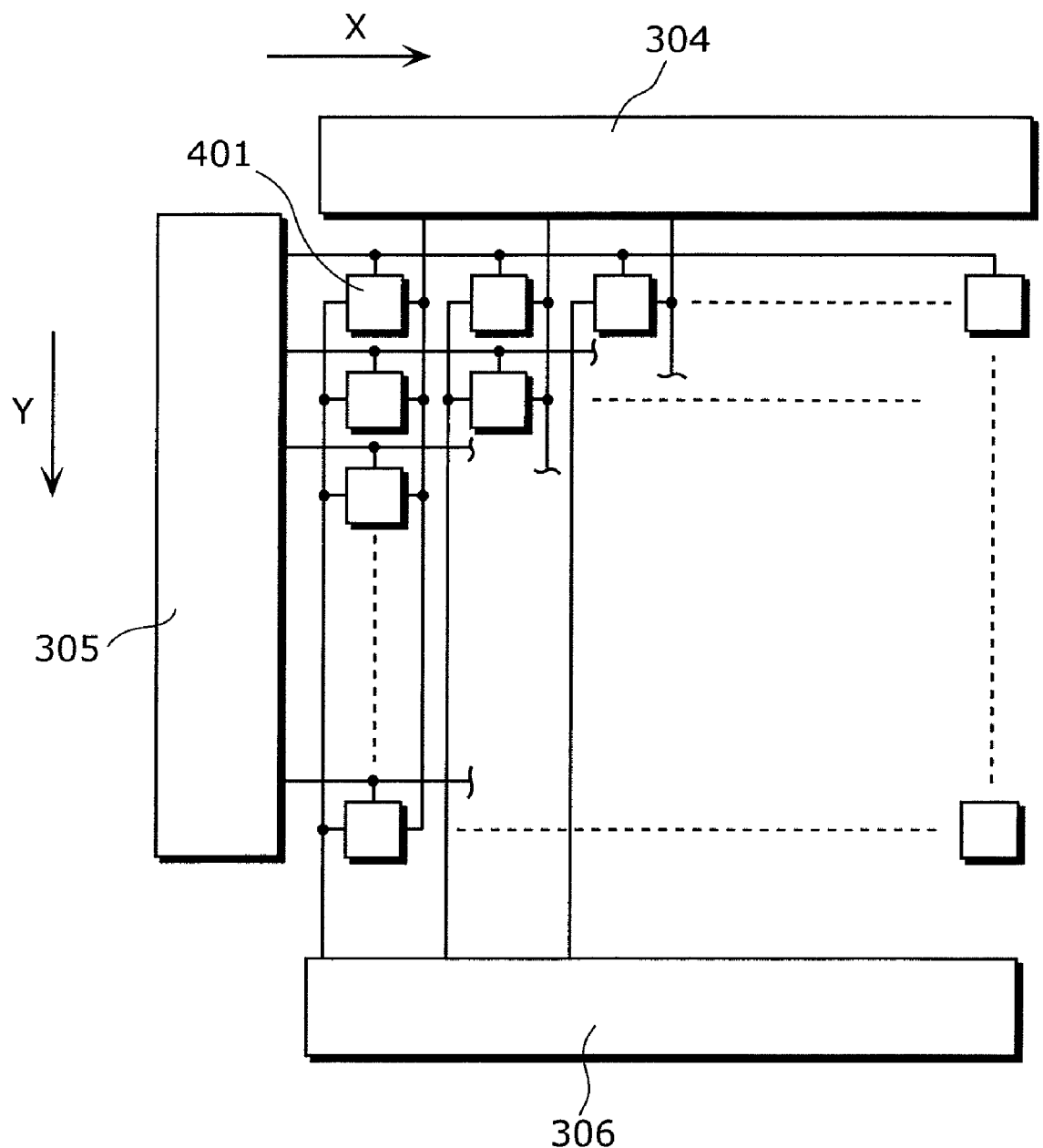
FIG. 4 illustrates a circuit configuration of the image sensor according to the embodiment 1.
Figure 5:
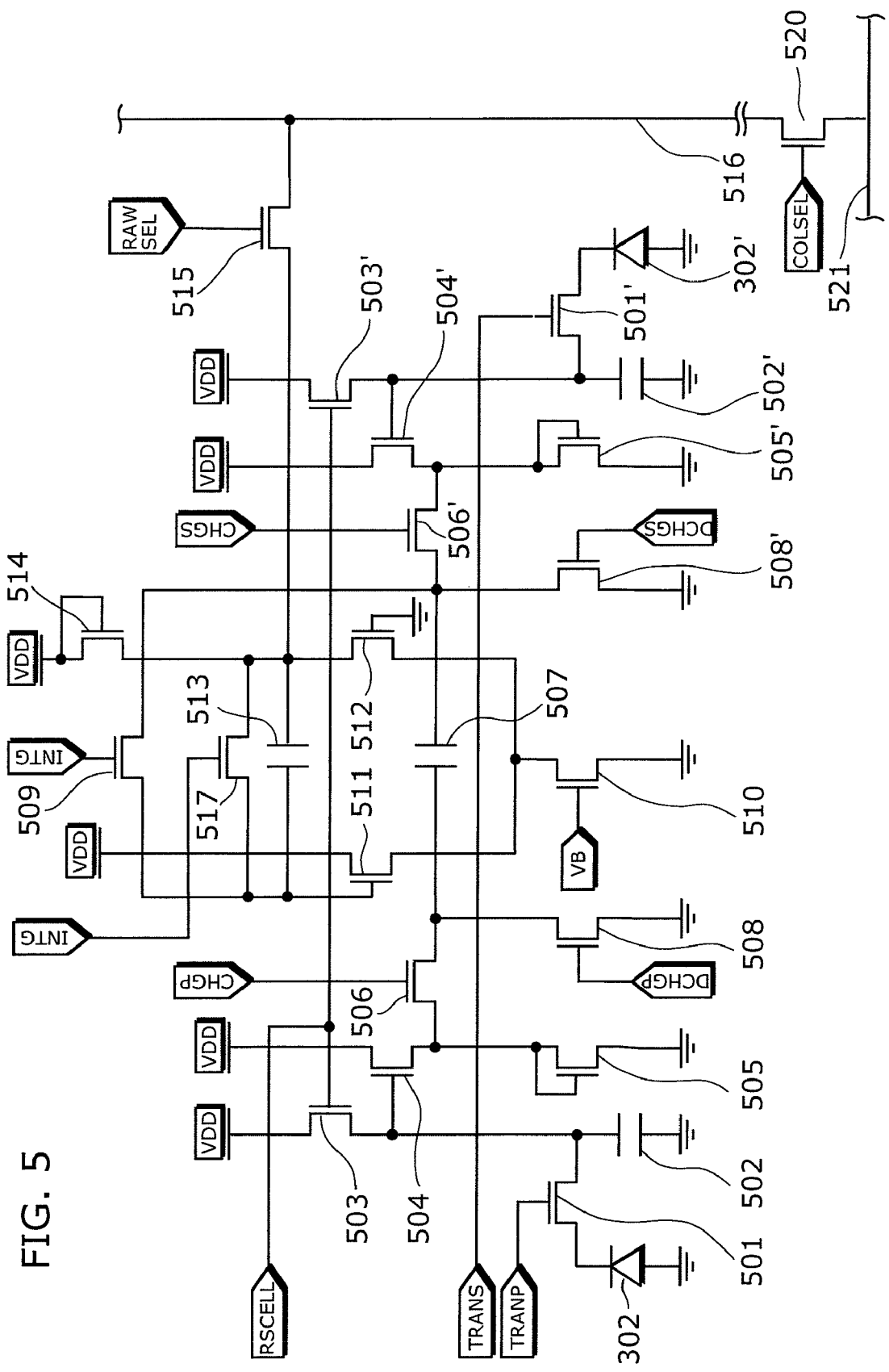
FIG. 5 illustrates a detailed circuit configuration in a pixel of the image sensor according to the embodiment 1.

FIG. 4 illustrates a circuit configuration of the image sensor according to the embodiment 1, and FIG. 5 illustrates a detailed circuit configuration in a pixel 401. It is to be noted that a coordinate system in FIG. 4 is equal to the one in FIG. 3.

In the image sensor, pixels 401, each of which includes one pair of photodiodes, are arranged two-dimensionally, and driving signals from the signal process driving circuit 304, the row scanning circuit 305, and the column scanning circuit 306 are distributed to each pixel 401 via signal lines. A pixel including the photodiodes 302 and 302' of FIG. 3 is an example of a pixel unit in the present invention, and is indicated as the pixel 401.

The photodiodes 302 and 302' form a pair, and a readout circuit connected to the pair of photodiodes reads signals of the pair of photodiodes and outputs the read signals. The readout circuit includes transfer gates 501 and 501', floating diffusion amplifiers 502 and 502', reset transistors 503 and 503', source follower amplifiers 504 and 504', load transistors 505 and 505', and transistors 506 and 506'.

In the readout circuit, TRANP and TRANS signals generated by the signal process driving circuit 304 put the transfer gates 501 and 501' into conduction state. A reset signal RSCELL from the signal process driving circuit 304 puts the reset transistors 503 and 503' connected to the transfer gates 501 and 501' into conduction state, and the reset transistors 503 and 503' reset the floating diffusion amplifiers 502 and 502'. The transfer gates 501 and 501' transfer signal charges of the pair of photodiodes to the floating diffusion amplifiers 502 and 502' that are reset, and the source follower amplifiers 504 and 504' connected to the load transistors 505 and 505' make the signal charges readable as voltage signals, that is, a voltage output condition. Reading start signals CHGP and CHGS from the signal process driving circuit 304 provides voltage outputs to a difference circuit via the transistors 506 and 506'.

The difference circuit is a circuit which outputs a difference signal corresponding to a difference between the signal read from the photodiode 302 and the signal read from the photodiode 302'. The difference circuit has one terminal connected to the photodiode 302 and the other terminal connected to the photodiode 302', and includes a capacitor 507 connected to the readout circuit.

It is to be noted that the capacitor 507 is an example of a first capacitor in the present invention.

In the difference circuit, the signal read from the photodiode 302 and the signal read from the photodiode 302' are outputted to respective terminals of the capacitor 507. The capacitor 507 is charged with a voltage equivalent to the difference signal between the photodiodes 302 and 302'. After the capacitor 507 is charged, the transistors 506 and 506' are put into off-state. An integration circuit included in a differential input amplifier in a subsequent stage integrates the difference signal between the photodiodes 302 and 302' that is accumulated in the capacitor 507 as mentioned above. The following describes a configuration and operations of the integration circuit.

The integration circuit is a circuit which outputs, as a pixel signal, a difference signal on which integration is performed, and includes transistors 508, 508', and 509, a differential amplifier, and a feedback capacitor 513 inserted between an input terminal and an output terminal of the differential amplifier. The differential amplifier includes an operational amplifier having differential input stage transistors 511 and 512 connected in series with a transistor 510 as an input stage, the transistor 510 is biased with a constant bias voltage VB and performs a constant current operation. That is to say, the differential amplifier includes the operational amplifier having one input terminal connected to an output of the difference circuit and the other input terminal connected to constant potential.

In the integration circuit, when an INTG signal obtained from the signal process driving circuit 304 puts the transistor 509 into on-state and a DCHGP signal obtained from the signal process driving circuit 304 puts the transistor 508 into on-state, charges charged at a terminal opposite to a terminal connected to the transistor 508 of the capacitor 507 are completely transferred to the feedback capacitor 513 by a virtual ground operation and a principle of conservation of charge of the differential amplifier. Repeating this operation allows the feedback capacitor 513 to repeatedly accumulate and integrate the difference signal between the photodiodes 302 and 302'. A source side voltage of a load transistor 514 which varies depending on an amount of charge to be accumulated in the feedback capacitor 513 is outputted as a pixel signal. After performing difference and integration operations for a predetermined number of times, a column selection signal RAWSEL generated from the row scanning circuit 305 puts a transistor 515 into on-state. As a result, the pixel signal is outputted to a column signal output line 516 (vertical output line) connected to the column scanning circuit 306 via the transistor 515. Subsequently, a row selection signal COLSEL puts a transistor 520 into on-state, the pixel signal outputted to the column signal output line 516 is sequentially outputted, on a pixel-by-pixel basis, to a horizontal signal output line 521 in a subsequent stage via the transistor 520.

Figure 6:
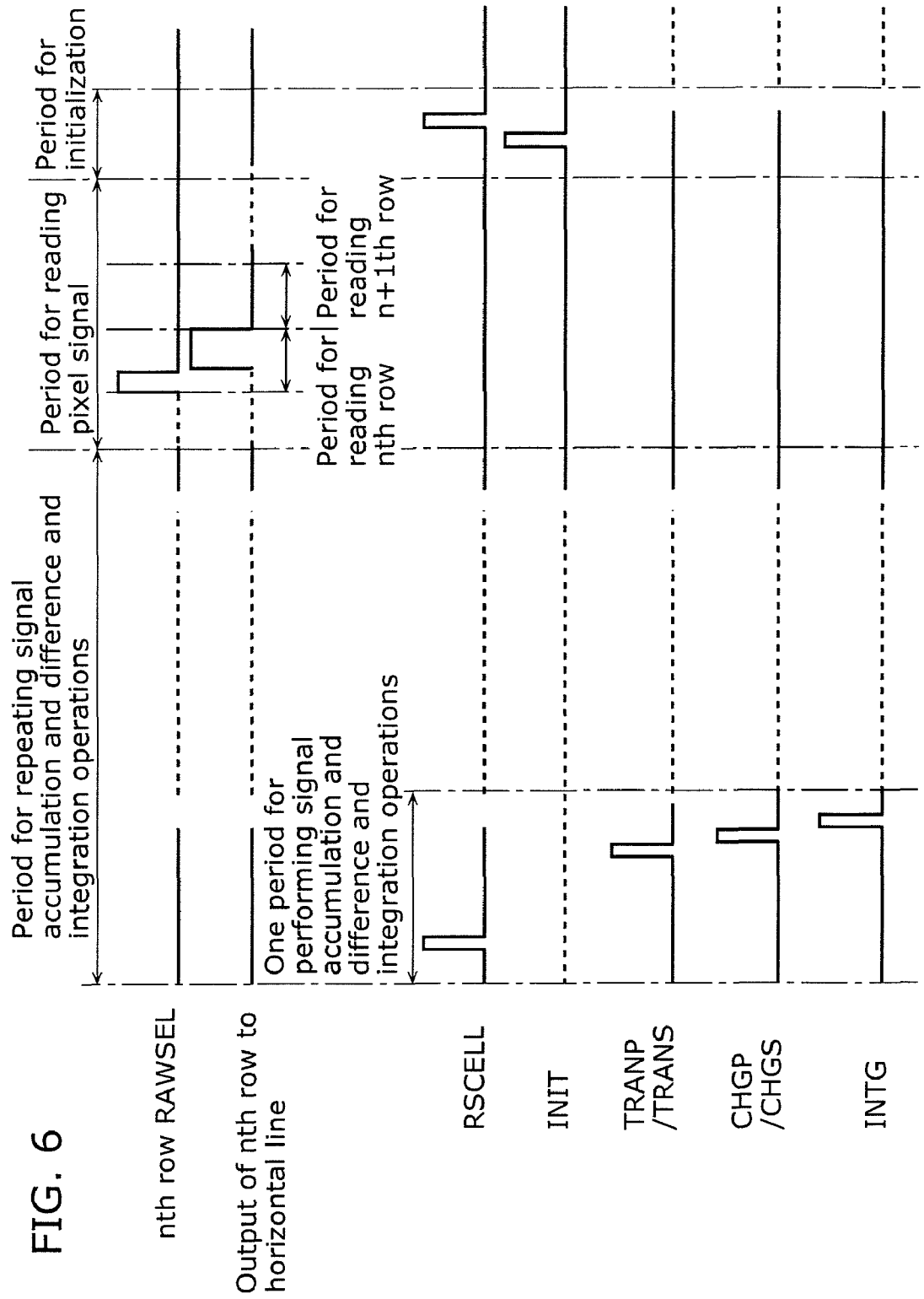
FIG. 6 is an example of a timing chart illustrating operations of the image sensor according to the embodiment 1.

FIG. 6 is an example of a timing chart illustrating operations of the image sensor having the circuit configurations shown in FIGS. 4 and 5.

Generation of a pixel signal for one pixel, that is, reading a signal from a photodiode, generation of a difference signal, and integration of the difference signal are performed within a time of accumulating data for one frame image. After a period during which a difference between signals of the photodiodes 302 and 302' (difference signal) is calculated and the calculated difference signal is integrated for a predetermined number of times (period for repeating signal accumulation and difference and integration operations), a period during which the integrated difference signal (pixel signal) is read from a pixel (period for reading pixel signal) is established. This allows two-dimensional frame image data to be outputted without overlapping the period for difference and integration operations with the period for reading pixel signal.

After the completion of each operation, the DCHGP signal shorts out both ends of the capacitor 507 to ground so as to initialize the capacitor 507. In addition, after the period for reading pixel signal, an INIT signal provided from the signal process driving circuit 304 initializes the feedback capacitor 513. According to the above-mentioned configuration, it is possible to calculate the difference between the signals (difference signal) and integrate the calculated difference signal in each pixel, and then output data for one frame image having the integrated signal as a pixel signal.

Embodiment 2

The following describes an image sensor according to an embodiment 2 of the present invention with reference to FIGS. 7 to 10.

Figure 7:
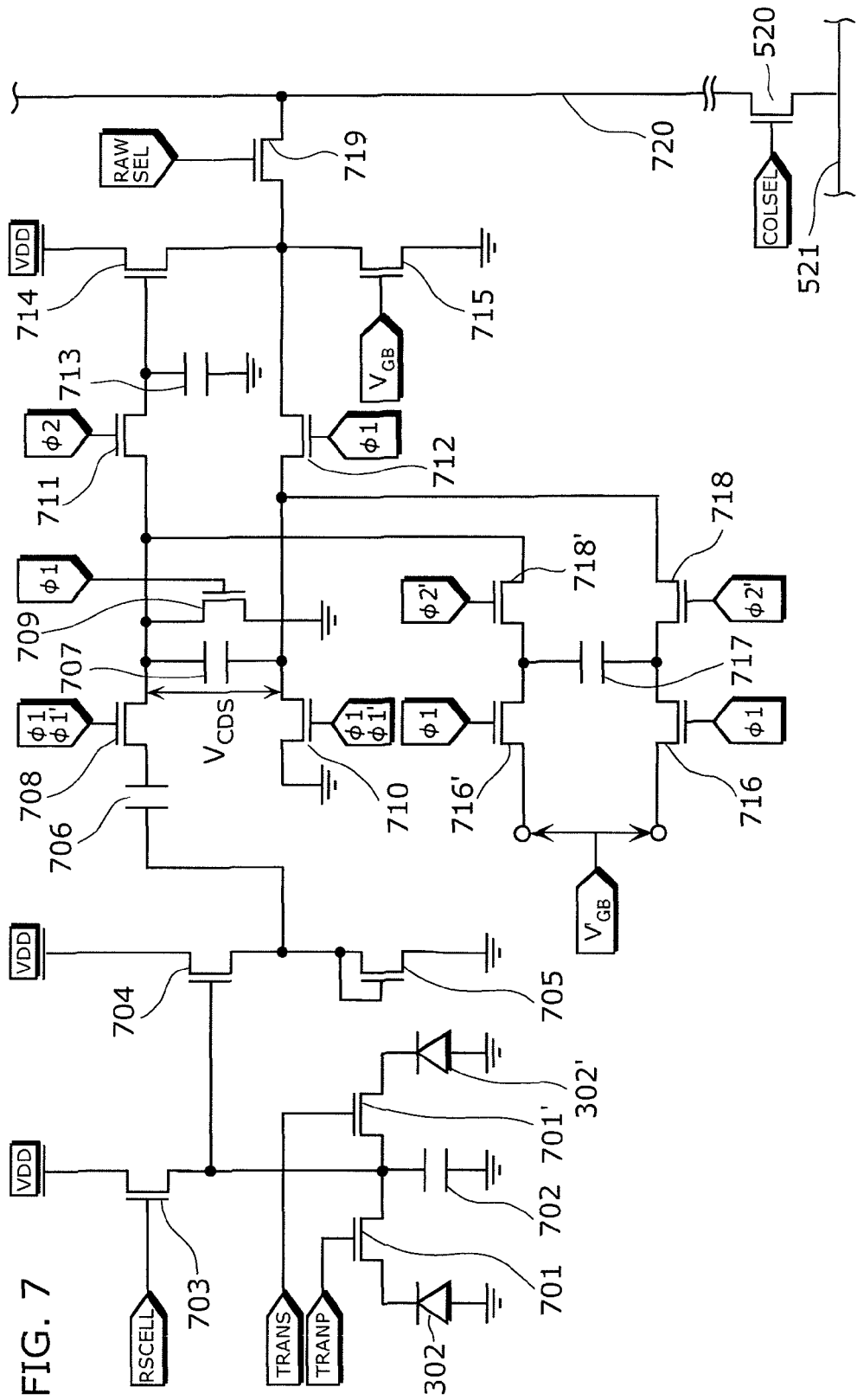
FIG. 7 illustrates a detailed circuit configuration in a pixel of an image sensor according to an embodiment 2 of the present invention.

FIG. 7 illustrates a detailed circuit configuration in a pixel of the image sensor according to the embodiment 2. It is to be noted that FIG. 7 illustrates a circuit configuration in a pixel including the photodiodes 302 and 302' of FIG. 3.

Also in the image sensor according to the embodiment 2, a polarized light filter is arranged for each pair of photodiodes in the same manner as in the image sensor of FIG. 3, and the signal process driving circuit 304, the row scanning circuit 305, and the column scanning circuit 306 are arranged around a pixel region where the plural pixels are arranged two-dimensionally as shown in FIG. 4. In contrast, what differs from the image sensor according to the embodiment 1 are a readout circuit which reads signals of the pair of photodiodes in the pixel, a difference circuit which calculates a difference, and an integration circuit which integrates the difference.

The photodiodes 302 and 302' form a pair, and a readout circuit connected to the pair of photodiodes reads signals of the pair of photodiodes and outputs the read signals. The readout circuit includes transfer gates 701 and 701', a floating diffusion amplifier 702, a reset transistor 703, a source follower amplifier 704, and a load transistor 705.

The pair of photodiodes shares the floating diffusion amplifier 702 and the source follower amplifier 704 for reading a signal. Accordingly, in the readout circuit, the signals of the photodiodes 302 and 302' are sequentially outputted in a time division manner. The TRANP and TRANS signals generated from the signal process driving circuit 304 put the transfer gates 701 and 701' connected to the pair of photodiodes into conduction state. The reset signal RSCELL from the signal process driving circuit 304 puts the reset transistor 703 into conduction state, and the reset transistor 703 resets the floating diffusion amplifier 702. A signal charge of the photodiode 302 is transferred to the floating diffusion amplifier 702 that is reset, the source follower amplifier 704 connected to the load transistor 705 makes the signal charge readable as a voltage signal, that is, a voltage output condition. The voltage output is provided to a difference circuit which calculates a difference and an integration circuit which integrates the difference, the difference circuit and the integration circuit being in a subsequent stage. Subsequently, with the same operation, a signal charge of another photodiode 302' is outputted to the difference circuit and the integration circuit.

In the image sensor according to the embodiment 2, as the difference circuit for obtaining the difference between two signals of the photodiodes 302 and 302' which are sequentially outputted as time series signals in the manner mentioned above, a correlated double sampling circuit using charge capacity division to two capacitors 706 and 707 which are connected in series is used. The correlated double sampling circuit includes switch transistors 708, 709, and 710, and the capacitors 706 and 707.

It is to be noted that the capacitor 707 is an example of a fourth capacitor in the present invention.

A clock signal $\phi1$ provided from the signal process driving circuit 304 puts the switch transistors 708 and 709 into conduction state. A voltage signal of the photodiode 302 outputted ahead by the source follower amplifier 704 is clamped to the capacitor 706. A clock signal $\phi1'$ provided from the signal process driving circuit 304 puts the switch transistors 708 and 710 into conduction state. When a voltage signal of the photodiode 302' is subsequently outputted, a voltage $V_{CDS}$ proportional to the difference between output signals of the photodiodes 302 and 302' is sample-held in the capacitor 707. The difference circuit employing a correlated double sampling system in which a series capacitor is used has been conventionally applied as a noise canceller circuit of a CMOS sensor (for example, see Non-patent Reference 5: J. Hynecek, IEEE Trans. Electron Devices, Vol. 37, No. 10, pp. 2193-pp. 2200, (1990)). In the application, however, the difference circuit is arranged outside of the pixel region of the image sensor in the application. Specifically, the difference circuit is arranged in a signal processing circuit connected to the column signal output line (vertical signal line). Accordingly, to reduce an influence of wiring capacity of a horizontal signal output line provided in a subsequent stage of the signal processing circuit, it is necessary to set a capacitance value of two capacitors used in the difference circuit itself to more than 1 pF, a huge value, and the difference circuit occupies a redundant portion of an area of an entire chip. On the other hand, since the difference circuit is arranged in each pixel in the image sensor according to the embodiment 2, there is no influence of large wiring capacitance caused by a horizontal output circuit and the like, the maximum value of capacitance of the difference circuit is reduced to below 0.4 pF, and the above-mentioned redundancy in the chip area is removed.

In the image sensor according to the embodiment 2, the integration circuit in a subsequent stage of the correlated double sampling circuit integrates the difference signal between the two photodiodes which is accumulated in the capacitor 707 as mentioned above. The integration circuit is a circuit which outputs, as the pixel signal, the difference signal which is integrated, and includes switch transistors 711 and 712, capacitors 713 and 717, transistors 714, 716, 716', 718, 718', and 719, and a load transistor 715. In the integration circuit, the difference signal of the capacitor 707 is inputted as a gate-to-source voltage of the transistor 714.

It is to be noted that, in the present invention, the transistor 714 is an example of a first transistor, the capacitor 717 is an example of a fifth capacitor, and the capacitor 713 is an example of a second capacitor.

When a clock signal $\phi 2$ having a different phase from the above-mentioned clock signal and provided from the signal process driving circuit 304 puts the switch transistors 711 and 712 into on-state, the capacitor 707 is connected to the gate-to-source of the transistor 714 included in the second source follower amplifier having a constant current load. At this time, the capacitor 713 is inserted to gate-to-ground of an input stage of the transistor 714, and a signal proportional to a signal of the capacitor 707 is accumulated in the capacitor 713. Here, the transistor 714 is connected in series with the load transistor 715 biased with a constant bias voltage $V_{GB}$, and a drain current of the transistor 714 is equally constant to a drain current of the load transistor 715. Accordingly, a voltage value proportional to an amount of signal accumulation of the capacitor 713 is obtained as an output voltage of the integration circuit. Hereafter, repeating this operation allows the difference signal between the photodiodes 302 and 302' to be accumulated in the capacitor 713. Here, the capacitor 717 charged with a constant voltage $V_{GB}'$ is connected in parallel with the capacitor 707 where the signal of the photodiode 302 is accumulated at the timing of clamping the signal of the photodiode 302 to the capacitor 713. At this time, the constant voltage $V_{GB}'$ is lower than a threshold voltage of the transistor 714. A bias necessary for the transistor 714 to operate in a saturated region is charged to a gate of the transistor 714 with a voltage charged to the capacitor 717, and the difference signal of the photodiodes 302 and 302' is surely charged to the capacitor 713. When capacitance values of the capacitors 707, 713, and 717 are $C_i$, $C_a$, and $C_B$, respectively, the bias voltage of the load transistor 715 is $V_{GB}$, a charging voltage of the capacitor 717 is $V_{GB}'$, an output signal of the transistor 714 before the clock signal $\phi 2$ is inputted and an output signal of the transistor 714 after the clock signal $\phi 2$ is inputted are $V_{o, n-1}$, and $V_{o, n}$, respectively, a charging voltage of the capacitor 707 is $V_{i, n-1}$, and a threshold voltage of the transistor 714 and the load transistor 715 is $V_T$, k values each is $k_1$ and $k_2$, a general solution can be expressed as the following equation:

[Equation 1]

$$V_{o,n} = V_{o,n-1} + \frac{C_B}{C_a} V_{GB}' + \frac{C_i}{C_a} V_{i,n-1} - \frac{C_i + C_B}{C_a} \left\{ \sqrt{\frac{k_2}{k_1}} (V_{GB} - V_T) + V_T \right\} \quad (1)$$

Thus, when the charging voltage $V_{GB}'$ of the capacitor 717 is set to satisfy a relationship of the following equation (2), it is possible to accurately cancel an offset voltage of an output resulting from the bias voltage $V_{GB}$ of the load transistor 715.

[Equation 2]

$$V_{GB}' = \frac{C_i + C_B}{C_B} \sqrt{\frac{k_2}{k_1}} V_{GB} \quad (2)$$

Further, when the capacitance value $C_i$ of the capacitor 707 is larger than the capacitance value $C_a$ of the capacitor 713, a coefficient $C_i/C_a$ of the voltage $V_{i, n-1}$ becomes larger than 1. Consequently, it is possible to not only integrate but also amplify the difference signal.

The integration circuit using such a switched capacitor and source follower amplifier has been reported in Non-patent Reference 6: S. C. Fan, R. Gregorian, G. C. Temes and M. Zomorrdi, Proc. IEEE Int. Symp. Circuits and Systems, pp. 334-pp. 337, (1980). The integration circuit has the same circuit configuration as the integration circuit of FIG. 7, and all of the capacitance values of the capacitors 707, 713, and 717 are equal. However, there exists a problem in mere application of the above circuit configuration to the present embodiment. Since drain voltages of the switch transistors 711 and 712 and the transistors 718 and 718' are different from each other, ON resistance of each transistor is different from each other. Accordingly, when the switch transistors 711 and 712 and the transistors 718 and 718' all together are in the transition to on-state at a time of inputting the clock signal $\phi 2$, a terminal voltage of the capacitor 713, that is, a gate voltage of the transistor 714 becomes unstable and excess noise may be generated. In order to solve such a problem, in the integration circuit of the image sensor according to the embodiment 2, the noise is reduced by delaying the timing of inputting the charging voltage of the capacitor 717 to the integration circuit and the timing of inputting the difference signal to the integration circuit. That is to say, the transistors 718 and 718' are driven with a clock signal $\phi 2'$ having a phase different from the phase of the clock signal $\phi 2$, and the noise is reduced by causing transistors connected to the same node to make the transition simultaneously.

It is to be noted that although one end of the capacitor 713 is connected to ground, it may be connected to a predetermined fixed potential. In this case, it is possible to set a bias to be applied to the gate of the transistor 714.

Figure 8:
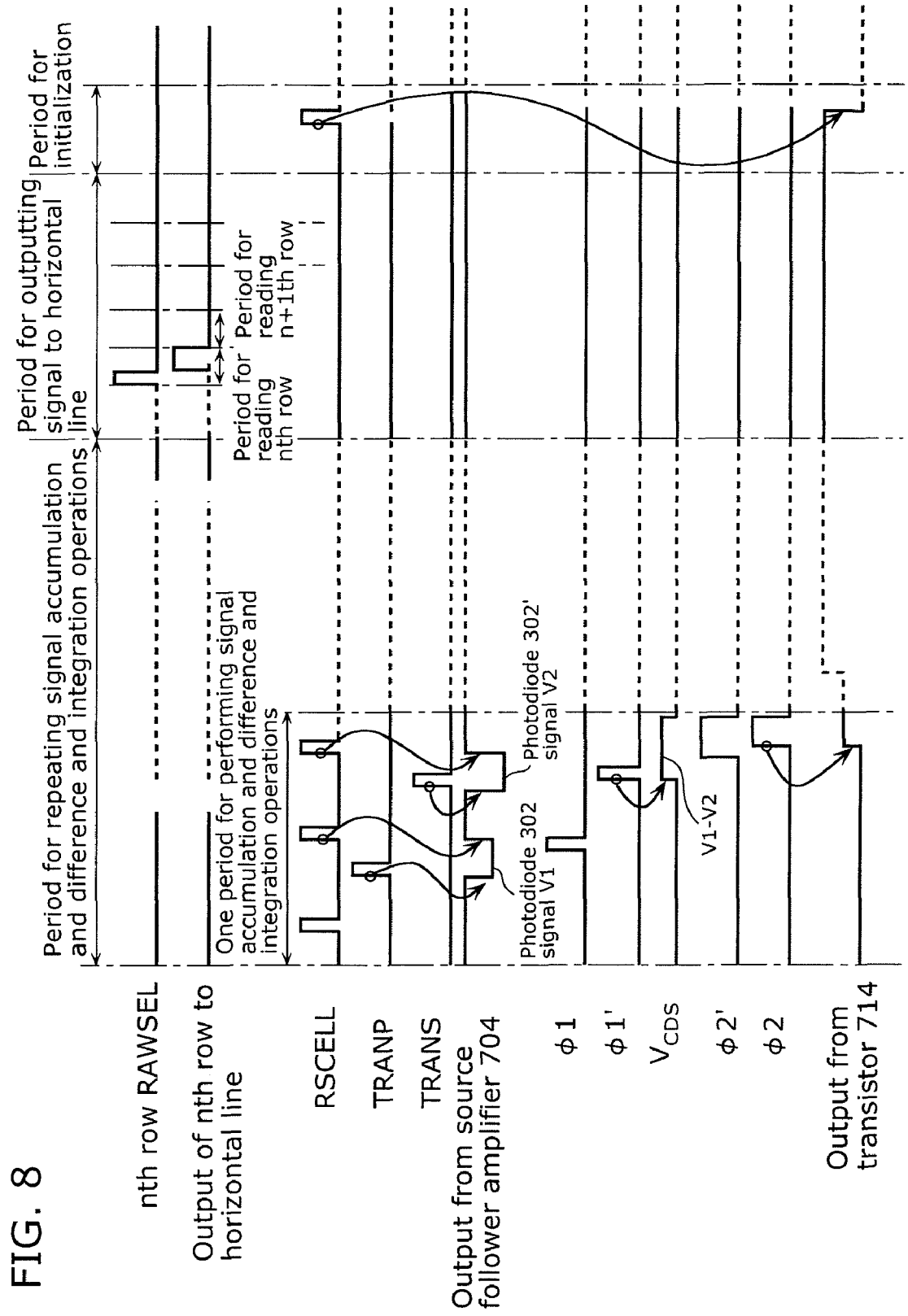
FIG. 8 is an example of a timing chart illustrating operations of the image sensor according to the embodiment 2.

FIG. 8 is an example of a timing chart illustrating operations of the image sensor having the circuit configuration of FIG. 7.

Generation of a pixel signal for one pixel, that is, reading of a signal from a photodiode, generation of a difference signal, and integration of the difference signal are performed within a time of accumulating data for one frame image. After a period during which a difference between signals of the photodiodes 302 and 302' (difference signal) is calculated and the calculated difference signal is integrated for a predetermined number of times (period for repeating signal accumulation and difference and integration operations), a period during which the integrated difference signal (pixel signal) is read from a pixel (period for reading pixel signal) is established. This allows the integrated difference signal (pixel data) to be outputted to the horizontal signal output line 521 via the column signal output line 720 (vertical signal line) and the transistor 520 at the timing at which a RAWSEL signal and a COLSEL signal rise simultaneously in each pixel. With this structure, similar to the image sensor according to the embodiment 1, it is possible to output two-dimensional frame image data without overlapping the period for difference and integration operations with the period for reading the pixel signal.

Figure 9:
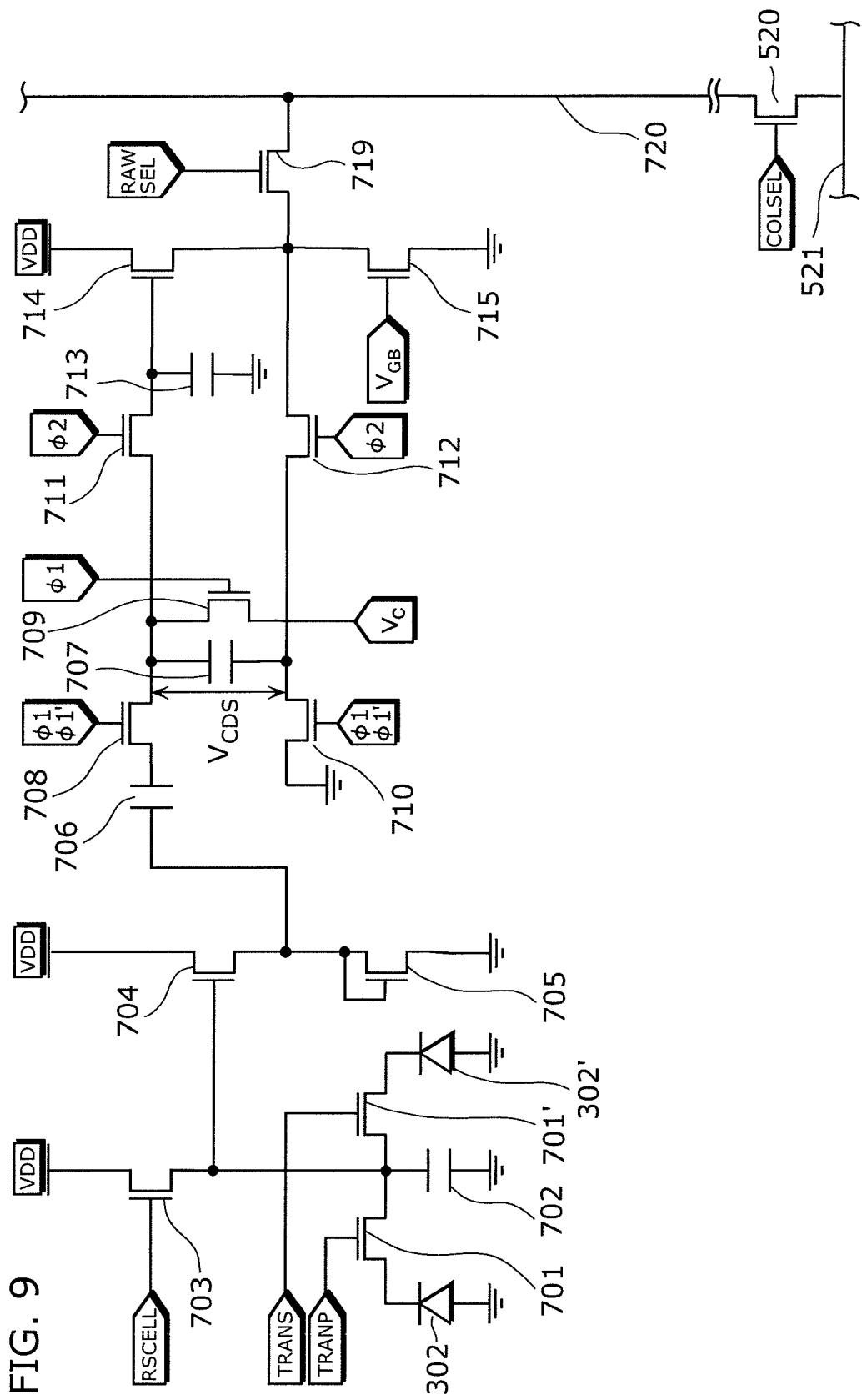
FIG. 9 illustrates a detailed circuit configuration in a pixel of a modification of an image sensor according to the embodiment 2.

FIG. 9 illustrates a detailed circuit configuration in a pixel of a modification of the image sensor according to the embodiment 2.

Also in the image sensor, the integration circuit in a subsequent stage of the correlated double sampling circuit integrates the difference signal between the two photodiodes which is stored in the capacitor 707. The integration circuit is a circuit which outputs, as the pixel signal, the difference signal which is integrated, and includes the switch transistors 711 and 712, the capacitor 713, the transistors 714 and 719, and the load transistor 715.

In the image sensor, the capacitor 717 which inputs a bias is not included in comparison to the circuit shown in FIG. 7. Avoidance of the structure where plural transistors are connected to the same node allows an instable operation of the transistor 714 as mentioned above to be avoided. In the circuit shown in FIG. 9, it is possible to input a bias voltage necessary for driving the transistor 714 as a voltage of a terminal opposite to a signal input terminal of the capacitor 706 connected to ground. It is assumed that capacitance values of the capacitors 706 and 707 are $C_c$ and $C_s$, respectively, that the first signal of a voltage value $V_1$ (signal of the photodiode 302) is inputted to the signal input terminal of the capacitor 706 when the clock signal $\phi 1$ is inputted to the correlated double sampling circuit having these series capacitors, and that a clamp voltage $V_c$ is inputted to the terminal opposite to the signal input terminal of the capacitor 706. At this time, the clamp voltage $V_c$ is lower than the threshold voltage of the transistor 714. After the switch transistor 709 is put into off-state, when the second signal (signal of the photodiode 302') is inputted to the input terminal of the capacitor 706, a connection point voltage $V_{CDS}$ of the capacitors 706 and 707 becomes the following value:

[Equation 3]

$$V_{CDS} = V_C + \frac{C_c}{C_c + C_S}(V_1 - V_2) \quad (3)$$

Accordingly, in the Equation 1 where $V_{GB}'=0$, $V_i=V_{CDS}$, a value of $V_c$ is as following:

[Equation 4]

$$V_C = \frac{C_i + C_B}{C_i}\sqrt{\frac{k_2}{k_1}} V_{GB} \quad (4)$$

With this, it becomes possible to realize effects of the Equation 2 that the offset voltage of the output resulting from the bias voltage $V_{GB}$ of the load transistor 715 can be accurately canceled, without using a bias capacitor and a transistor which switches the bias capacitor, and to avoid an instable operation of a circuit. Further, it becomes possible to drastically reduce the number of circuit elements, and to design a sensor having smaller area.

Figure 10:
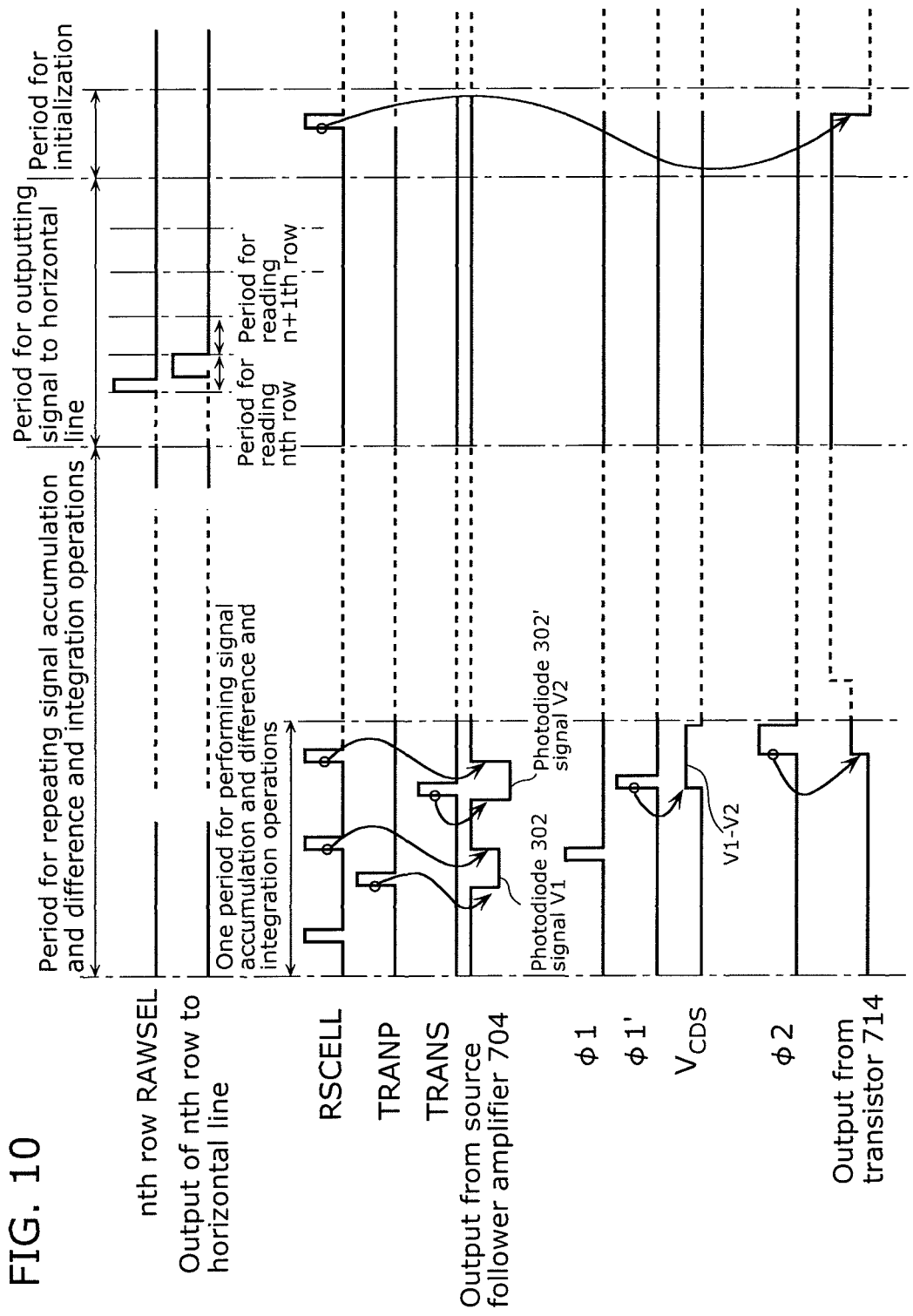
FIG. 10 is an example of a timing chart illustrating operations of a modification of an image sensor according to the embodiment 2.

FIG. 10 is an example of a timing chart illustrating operations of the image sensor having the circuit configuration shown in FIG. 9. It is to be noted that definitions of signal names are the same as in FIG. 8.

Generation of a pixel signal for one pixel, that is, reading of a signal from a photodiode, generation of a difference signal, and integration of the difference signal are performed within a time of accumulating data for one frame image. After a period during which the difference between the signals of the photodiodes 302 and 302' (difference signal) is calculated and the calculated difference signal is integrated for a predetermined number of times (period for repeating signal accumulation and difference and integration operations), a period during which the integrated difference signal (pixel signal) is read from the pixel (period for reading pixel signal) is established. This allows the integrated difference signal (pixel data) to be outputted to the horizontal signal output line 521 via the column signal output line 720 and the transistor 520 at the timing at which the RAWSEL signal and the COLSEL signal rise simultaneously in each pixel. With this structure, similar to the image sensor according to the embodiment 1, it is possible to output two-dimensional frame image data without overlapping the period for difference and integration operations with the period for reading pixel signal. Moreover, in comparison to the circuit shown in FIG. 7, the circuit shown in FIG. 9 has a margin in a driving timing since the clock signal $\phi 2'$ which switches the capacitor 717 for transistor bias can be omitted.

Embodiment 3

Figure 11:
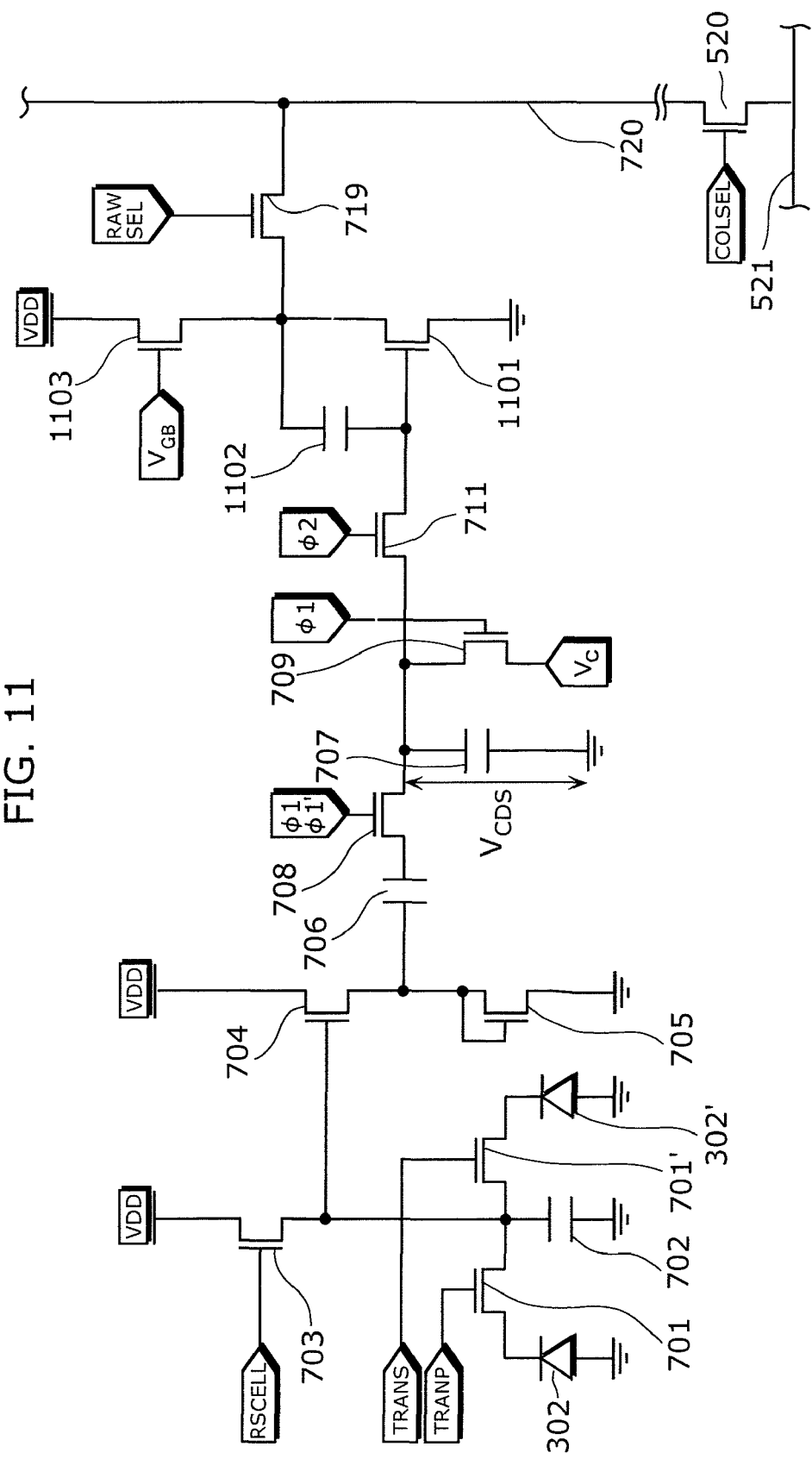
FIG. 11 illustrates a detailed circuit configuration in a pixel of an image sensor according to an embodiment 3 of the present invention.
Figure 12:
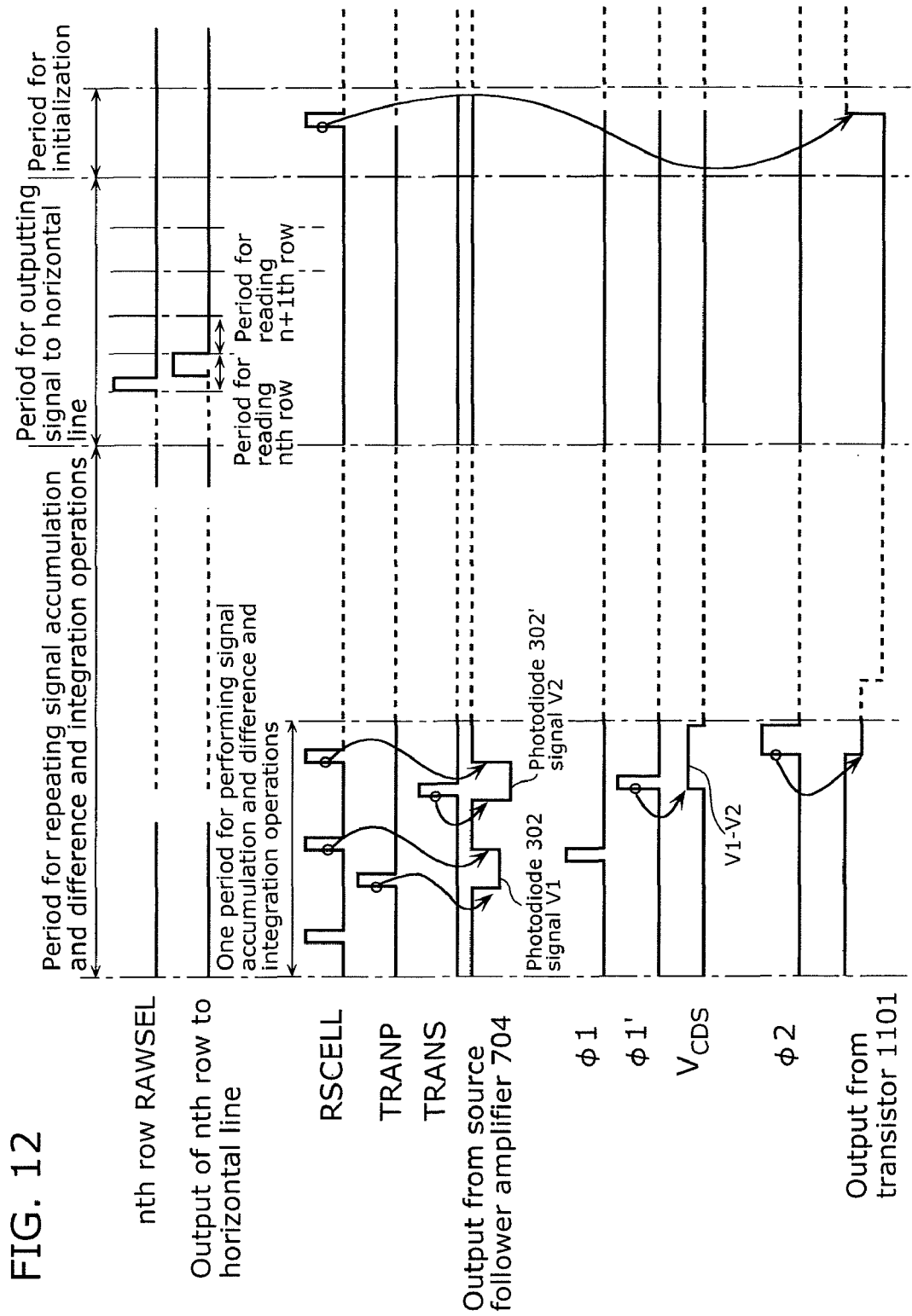
FIG. 12 is an example of a timing chart illustrating operations of the image sensor according to the embodiment 3.

The following describes an image sensor according to an embodiment 3 of the present invention with reference to FIGS. 11 and 12.

FIG. 11 illustrates a detailed circuit configuration in a pixel of the image sensor according to the embodiment 3. It is to be noted that FIG. 11 illustrates a circuit configuration in the pixel including the photodiodes 302 and 302' of FIG. 3.

Also in the image sensor according to the embodiment 3, a polarized light filter is arranged for each pair of photodiodes in the same manner as in the image sensor of FIG. 3, and the signal process driving circuit 304, the row scanning circuit 305, and the column scanning circuit 306 are arranged around a pixel region where the plural pixels are arranged two-dimensionally as shown in FIG. 4. In addition, a configuration of a readout circuit which reads a signal of the pair of photodiodes in the pixel is the same as in the image sensor according to the embodiment 2, and further a difference circuit obtaining a difference signal (difference between signals of the photodiodes) uses a correlated double sampling circuit and is the same as in the image sensor according to the embodiment 2. On the other hand, an integration circuit performing an integration operation is different from those in the embodiments 1 and 2.

In the image sensor according to the embodiment 3, the integration circuit in a subsequent stage of the correlated-double sampling circuit integrates the difference signal between the two photodiodes which is accumulated in the capacitor 707. The integration circuit is a circuit which outputs, as a pixel signal, the difference signal which is integrated, and includes the switch transistor 711, a capacitor 1102, transistors 719 and 1101, and a load transistor 1103. In the integration circuit, the difference signal is inputted as a gate-to-source voltage of the transistor 1101.

It is to be noted that, in the present invention, the transistor 1101 is an example of a second transistor, and the capacitor 1102 is an example of a third capacitor.

In the image sensor, with the same operations performed by the image sensor according to the embodiment 2, when the switch transistor 711 is put into on-state according to a clock signal φ2 which is provided from the signal process driving circuit 304 and which has a different phase, the capacitor 707 where the difference signal between the two photodiodes is accumulated is connected to gate-to-ground at the transistor 1101 of source ground. In this case, the capacitor 1102 is inserted to gate-to-drain of an input stage of the transistor 1101, and a signal charge proportional to a signal charge of the capacitor 707 is accumulated in the capacitor 1102. Here, the transistor 1101 is connected in series with the load transistor 1103 biased with a constant bias voltage $V_{GB}$. In addition, as in the image sensor of FIG. 9, a bias voltage necessary for an amplification operation is inputted, as a clamp voltage $V_c$, from a terminal opposite to a signal input terminal of the capacitor 706 via a switching transistor 709 of the correlated double sampling circuit. Here, the clamp voltage $V_c$ is higher than a threshold voltage of the transistor 1101. A drain current of the transistor 1101 is equally constant to a drain current of the load transistor 1103. Accordingly, a voltage value proportional to an amount of charge of the capacitor 1102 is obtained as an output voltage of the integration circuit. Hereafter, repeating this operation allows the difference signal between the photodiodes 302 and 302' to be accumulated in the capacitor 1102.

It is to be noted that, as stated above, when a capacitance value of the capacitor 707 is larger than a capacitance value of the capacitor 1102, it is possible to not only integrate but also amplify the difference signal.

FIG. 12 is an example of a timing chart illustrating operations of the image sensor having the circuit configuration of FIG. 11. It is to be noted that the timing chart is almost the same as in FIG. 10. The difference is, however, that an output is performed not by the transistor 714 but by the transistor 1101. In addition, while a phase of an output voltage is in the same phase as an input voltage of a source follower amplifier in FIG. 10, the difference is a source ground amplifier circuit with a reverse phase output (increase in an input inverse proportion to decrease in a signal voltage) in FIG. 12.

Generation of a pixel signal for one pixel, that is, reading of a signal from a photodiode, generation of a difference signal, and integration of the difference signal are performed within a time of accumulating data for one frame image. After a period during which the difference between the signals of the photodiodes 302 and 302' (difference signal) is calculated and the calculated difference is integrated for a predetermined number of times (period for repeating signal accumulation and difference and integration operations), a period during which the integrated difference signal (pixel signal) is read from the pixel (period for reading pixel signal) is established. Here, an output voltage obtained from a drain of the transistor 1101 is outputted, as the pixel signal for one pixel, to the horizontal signal output line 521 via the column signal output line 720 and the transistor 520 at the timing at which the RAWSEL signal and the COLSEL signal that are obtained from the row scanning circuit 305 become on-state simultaneously. Setting the period for reading pixel signal for each row after the difference and integration operations are performed allows obtainment of data for one frame image in parallel with a signal output operation for one frame image.

Embodiment 4

Figure 13:
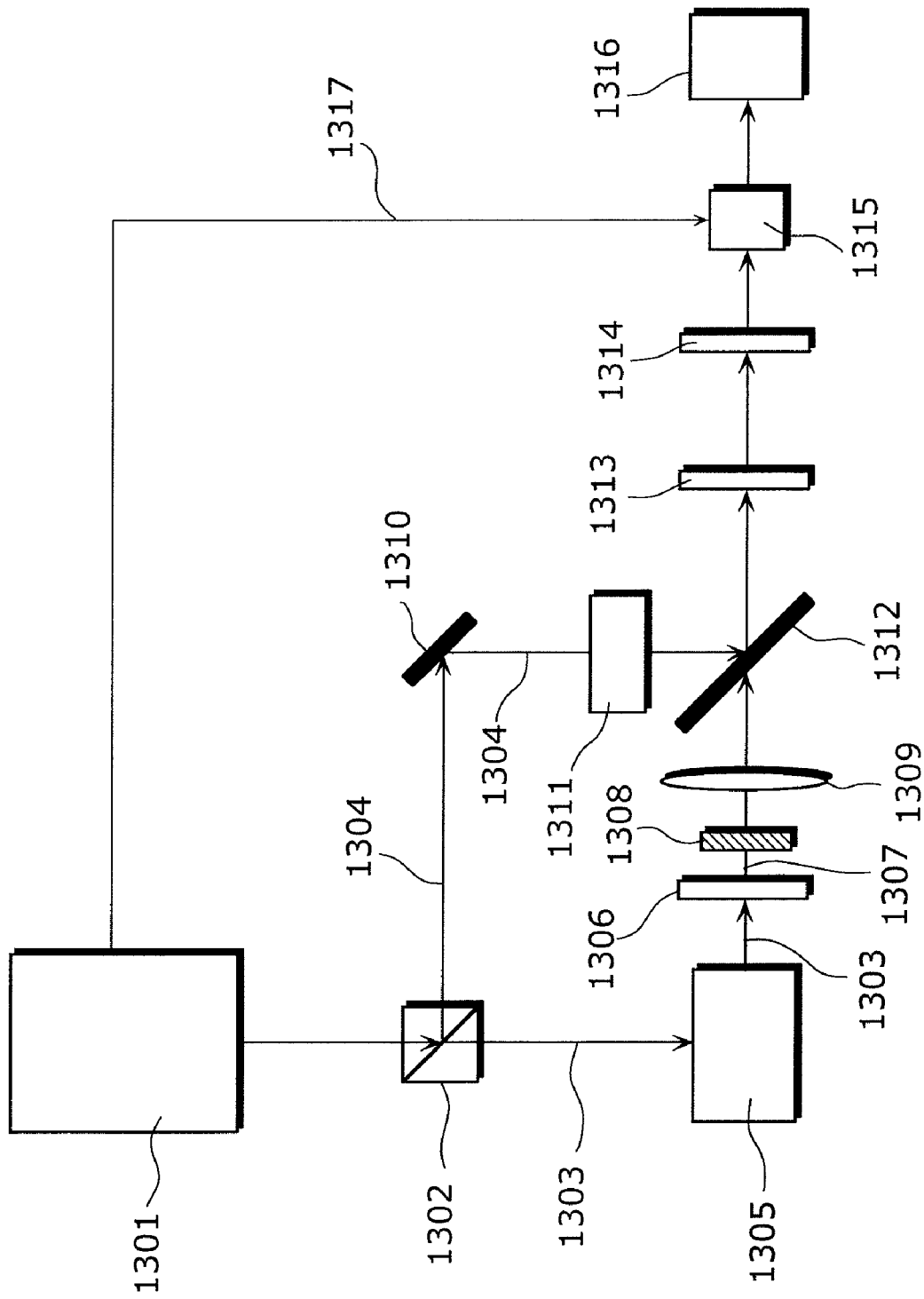
FIG. 13 schematically illustrates a structure of a THz electromagnetic radiation imaging device according to an embodiment 4 of the present invention.

FIG. 13 schematically illustrates a structural example of a THz electromagnetic radiation imaging device using the image sensor according to the embodiments 1 to 3.

The THz electromagnetic radiation imaging device includes an ultrashort pulsed light source 1301, a polarization beam splitter 1302, an optical delay line 1305, a THz electromagnetic radiation emitter 1306, a polyethylene lens 1309, a probe light course altering mirror 1310, a beam expander 1311, a silicon mirror 1312, an electric field modulator 1313, a ¼ wavelength plate 1314, an image sensor 1315, and an image reproduction device 1316.

It is to be noted that, in the present invention, the ultrashort pulsed light source 1301 is an example of a light source, and the THz electromagnetic radiation emitter 1306 is an example of an electromagnetic radiation source. Furthermore, in the present invention, the polyethylene lens 1309, the probe light course altering mirror 1310, the beam expander 1311, and the silicon mirror 1312 are an example of a superimposing optical element, and the electric field modulator 1313 is an example of an electro-optical modulation element.

In the THz electromagnetic radiation imaging device, the ultrashort pulsed light source 1301 generates ultrashort pulsed light with 100 fs pulse width at a frequency of 1 kHz, and the polarization beam splitter 1302 splits the ultrashort pulsed light into p-polarized light as pump light 1303 and s-polarized light as probe light 1304.

The pump light 1303 enters, via the optical delay line 1305, the THz electromagnetic radiation emitter 1306 which is structured with a photoconductive switch having an electrode pair formed on a semi-insulating GaAs wafer at an interval of 10 mm, and THz electromagnetic radiation 1307 is generated. The THz electromagnetic radiation 1307 generated in this manner is a beam having an extremely high collimating property, and is radiated to an object to be inspected 1308 having two-dimensional transmission distribution in a plane perpendicular to a traveling direction of the THz electromagnetic radiation 1307.

The THz electromagnetic radiation 1307 that transmitted through the object to be inspected 1308 becomes a spatially intensity-modulated beam with two-dimensional transmission characteristics of the object to be inspected 1308. The beam forms an image in an electric field modulator 1313 which is in a subsequent stage and which is made of a ZnTe crystal using the polyethylene lens 1309.

After the probe light course altering mirror 1310 alters a course of the probe light 1304 and further the beam expander 1311 expands a beam width of the probe light 1304, the probe light 1304 enters the silicon mirror 1312 made of silicon wafers and shares an optical axis with the intensity-modulated THz electromagnetic radiation 1307 that transmitted through the silicon mirror 1312. In other words, the probe light 1304 and the THz electromagnetic radiation 1307 are superimposed.

The superimposed probe light 1304 and THz electromagnetic radiation 1307 enter the electric field modulator 1313 made of a ZnTe crystal whose [110] plane is disposed perpendicular to the optical axis.

In a subsequent stage of the electric field modulator 1313, the ¼ wavelength plate 1314 and the image sensor 1315 described in the embodiments 1 to 3 are arranged in this order.

In the case where the THz electromagnetic radiation 1307 does not enter the electric field modulator 1313 simultaneously with each pulse of the probe light 1304, that is, in the case where a THz electromagnetic radiation pulse and a probe pulse are asynchronous, the ¼ wavelength plate 1314 sets the probe light 1304 to complete circular polarization state. At this time, since circular polarized light enters the image sensor 1315, a p-polarization component and an s-polarization component are equal to each other. Consequently, when the image sensor 1315 captures the probe light 1304, an equal amount of current is generated at a pair of photodiodes in each pixel in the image sensor 1315 and a signal charge is not accumulated in a floating diffusion amplifier.

On the other hand, in the case where the THz electromagnetic radiation pulse and the probe light pulse enter the electric field modulator 1613 simultaneously, that is, in the case where both of the pulses are synchronized, a specific physical quantity of the probe light 1304 is modulated according to an electric field of the THz electromagnetic radiation 1307 and, in comparison to the case where the THz electromagnetic radiation pulse and the probe light pulse are asynchronous, the polarization state of the probe light 1304 that transmitted through the electric field modulator 1313 undergoes polarizing axial rotation and further becomes elliptical polarized light. Accordingly, the polarization state of the probe light 1304 after transmitting through the ¼ wavelength plate 1314 does not become complete circular polarized light but elliptical polarized light. As a result, when the image sensor 1315 captures the probe light 1304, since the intensity of light entering the pair of photodiodes in each pixel in the image sensor 1315 differs and a different amount of current is generated, the signal charge is accumulated in the floating diffusion amplifier and a signal voltage, that is, a THz electromagnetic radiation detection signal is outputted.

The image reproduction device 1316 outputs the THz electromagnetic radiation detection signal (two-dimensional signal) detected with the above-mentioned principle. Thus, it is possible to perform THz electromagnetic radiation imaging on an object to be inspected having a high S/N ratio.

Moreover, in the image sensor according to the embodiment 4, a synchronizing signal 1317 synchronized with a pulse repetition period of the ultrashort pulsed light source 1301 is directly inputted to a signal process driving circuit of the image sensor 1315, and is a base clock of a reset signal. Such synchronization allows the image sensor 1315 to perform imaging synchronized with a pulse, and makes the image sensor 1315 perform a light receiving operation only in a period during which a laser light pulse enters the object to be inspected 1308, which can improve the S/N ratio. In addition, it becomes possible that the image sensor 1315 performs an integration operation on a difference signal as many times as the number of times a pulse is generated.

As stated above, although the image sensor and the electromagnetic radiation imaging device of the present invention have been described based on the embodiments, the present invention is not limited to the embodiments. Any modification conceived by a person with an ordinary skill in the art without departing from the gist of the present invention is included within the scope of the present invention.

Figure 14:
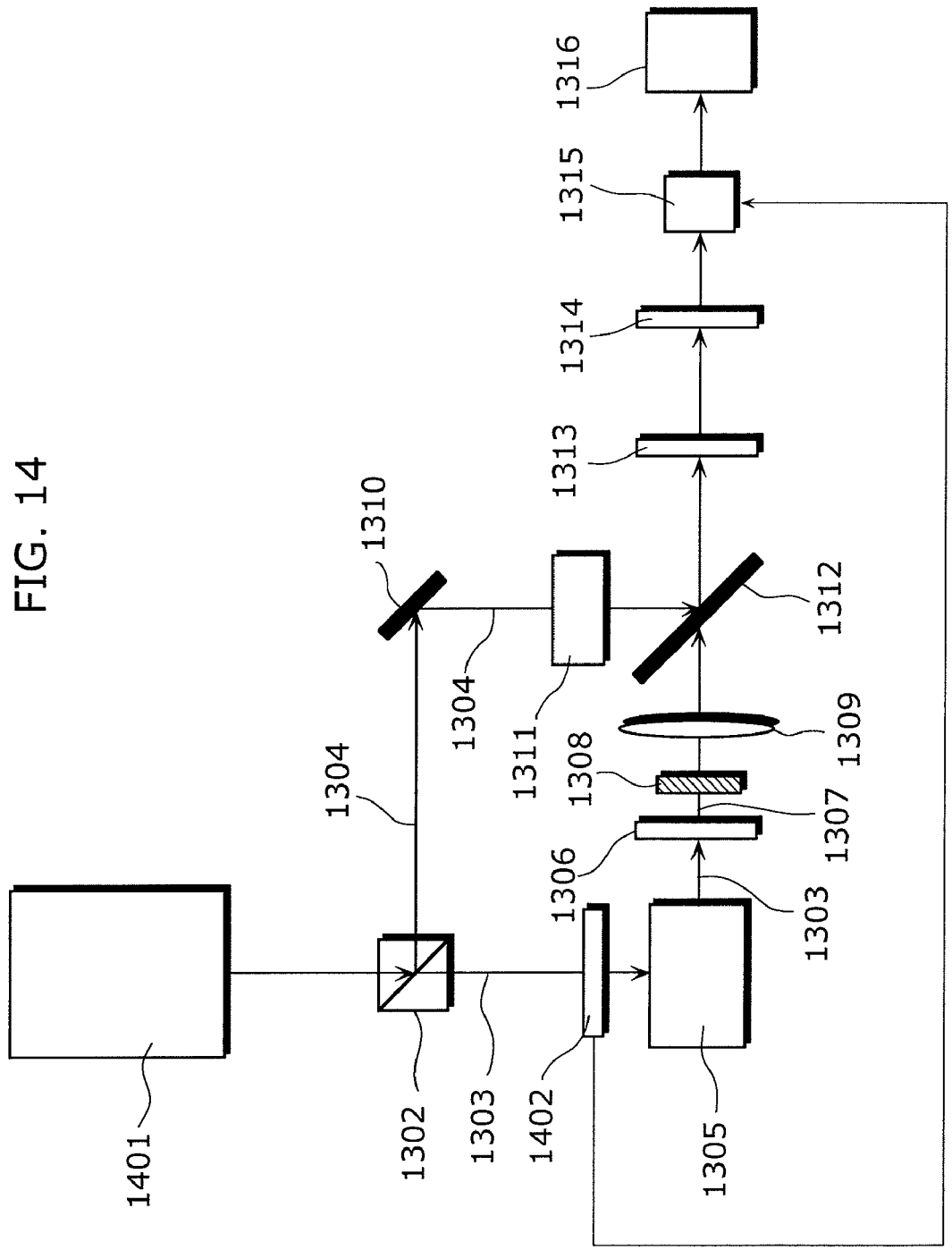
FIG. 14 schematically illustrates a structure of a modification of a THz electromagnetic radiation imaging device according to the embodiment 4.

For instance, in the THz electromagnetic radiation imaging device according to the embodiments, the pulse repetition period of the ultrashort pulsed light source is synchronized with the signal process driving circuit of the image sensor. It is, however, possible to perform the THz electromagnetic radiation imaging with the same principle in FIG. 13 by using a CW laser light source 1401 as a light source and providing a chopper 1402 as shown in FIG. 14. That is to say, it is also possible that the chopper 1402 intermittently chops the pump light 1303, and a period signal generated by the chopping is synchronized with a period signal of the signal process driving circuit of the image sensor.

Furthermore, in the image sensor according to the embodiments, the electric field modulator 1313 which modulates a polarization property is used, and the polarized light filters each having different transmission characteristics in which the maximum angle for passing polarized light differs, that is, the polarized light filer having different polarized light transmission characteristics is arranged on each pair of photodiodes. It is, however, possible to gain the equivalent effects even when an electric field modulator whose transmission wavelength characteristics vary with the THz electromagnetic radiation entering is used instead of the electric field modulator 1313 and a wavelength filter having a different transmission wavelength band region, that is, a wavelength filter having different wavelength transmission characteristics is arranged on the pair of photodiodes in the image sensor 1315.

In this case, the electric field modulator which modulates the transmission wavelength characteristics can be composed of a superlattice to which a thin film made of aluminum gallium arsenide and a thin film made of gallium arsenide are alternatively laminated. In addition, as the wavelength filter arranged on the pair of photodiodes, a wavelength filter having the maximum transmittance of 0.6 and half bandwidth of 20 nm is used. As described in Non-patent Reference 7: E. Hecht, "Optics", $4^{th}$ ed., p. 425-p. 430, Addison Wesley, San Francisco (2002), such a wavelength filter can be, for example, formed by providing, with photolithography, an interference filter made of a multilayer dielectric thin film to each photodiode.

Figure 15A:
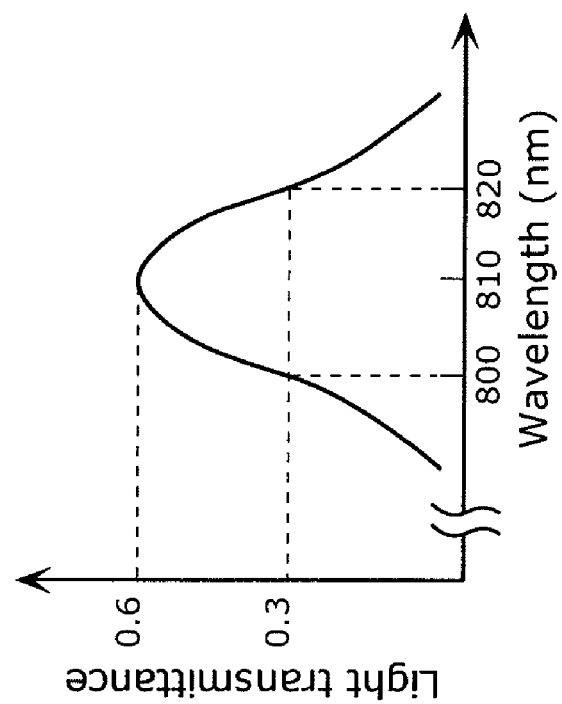
FIG. 15A is a diagram illustrating transmission characteristics of a wavelength filter used in a modification of an image sensor of the present invention.
Figure 15B:
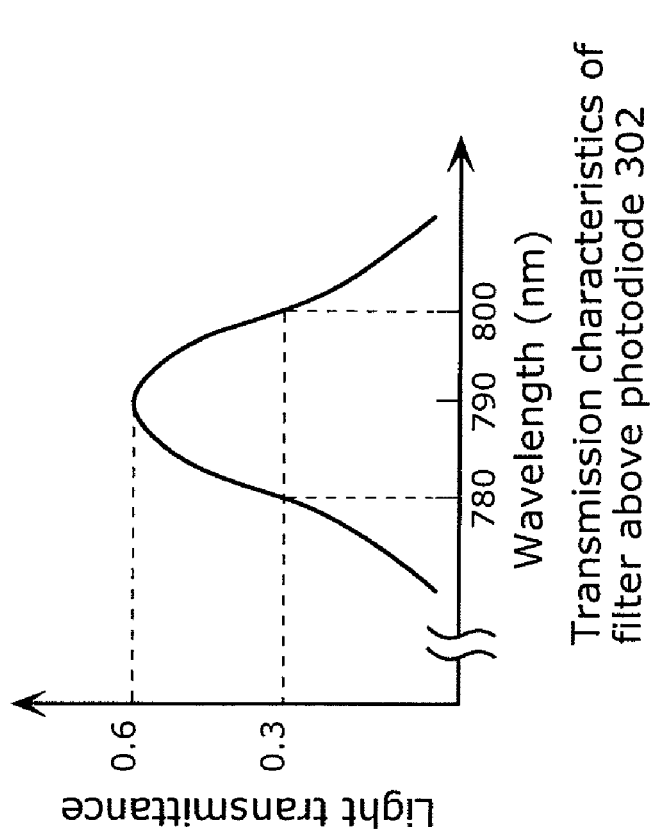
FIG. 15B is a diagram illustrating transmission characteristics of a wavelength filter used in a modification of an image sensor of the present invention.

For instance, two wavelength filters having transmission wavelength characteristics shown in FIGS. 15A and 15B are arranged above each photodiode. When light with 800 nm wavelength enters the image sensor having the wavelength filters, since the transmission wavelength characteristics of both wavelength filters are symmetrical with respect to the transmission peaks as the center, an amount of light transmitted through the wavelength filters is equal and an amount of photocurrent generated at the photodiodes 302 and 302' is also equal. Consequently, a net signal charge is not accumulated in the floating diffusion amplifier, and a signal output is not generated. On the other hand, in the case where the wavelength of the incident light is, for example, shifted 5 nm to a low wavelength side, an amount of light transmitted through the wavelength filter on the photodiode 302 increases and an amount of light transmitted through the wavelength filter on the photodiode 302' decreases. Accordingly, an amount of current generated at the photodiode 302 or 302' increases or decreases. For this reason, it becomes possible that a signal charge equivalent to a difference between the generated currents is accumulated in the floating diffusion amplifier as the net signal charge and the signal output is obtained.

As a result, the image sensor can be used as a wavelength shift monitor in the case where a central wavelength of the incident light is fixed in the image sensor and the central wavelength of the incident light is shifted by disturbance or other input signal as time passes.

Figure 16:
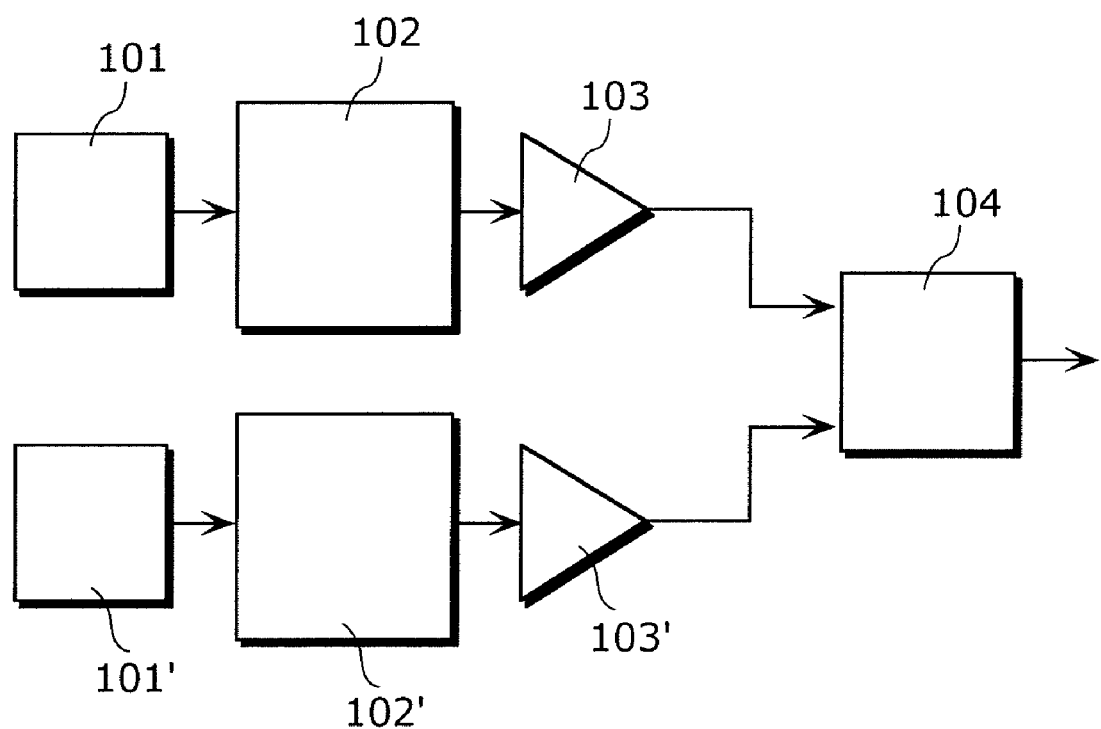
FIG. 16 is a circuit diagram illustrating an operating principle of a modification of an image sensor according to the present invention.

Furthermore, the integration circuit is provided for each pixel in the image sensor according to the embodiments. It may not be necessary to provide the integration circuit especially for each pixel as long as an amount of difference between signals of two photodiodes included in each pixel is large enough to be detected, and each pixel may have the circuit configuration shown in FIG. 16. That is to say, each pixel may have the circuit configuration in which the pair of adjacent photodiodes 101 and 101', the pair of readout circuits 102 and 102', the pair of signal output circuits 103 and 103', and the signal processing circuit 104 are included. In the circuit, the respective readout circuits 102 and 102' transfer signal charges accumulated by the photodiodes 101 and 101' to the signal output circuits 103 and 103' in the subsequent stage. Further, a signal output from each of the photodiodes 101 and 101' is inputted to the signal processing circuit 104 including the difference circuit in a subsequent stage.

Moreover, although the two photodiodes are included in one pixel in the image sensor according to the embodiments, the present invention is not limited to this, and three or more photodiodes may be included.

INDUSTRIAL APPLICABILITY

The present invention can be applied for an image sensor and an electromagnetic radiation imaging device, and especially for a security check device, a food inspection device, an atmospheric sensor, a medical diagnosis device, and the like.

What is claimed is:

1. An image sensor comprising a plurality of pixels arranged two-dimensionally,
    wherein each of said plurality of pixels includes:
        a first photodiode and a second photodiode, each of which generates a signal according to incident light;
        a readout circuit, connected to said first photodiode and said second photodiode, that reads the signal generated by said first photodiode and the signal generated by said second photodiode, and outputs the read signals; and
        a difference circuit, connected to said readout circuit, that receives the read signals from the readout circuit, and outputs a difference signal corresponding to a difference between the signal read from said first photodiode and the signal read from said second photodiode.

2. The image sensor according to claim 1,
    wherein each of said plurality of pixels further includes an integration circuit which integrates the difference signal and outputs the integrated difference signal as a pixel signal.

3. The image sensor according to claim 2,
    wherein said integration circuit includes an operational amplifier and a feedback capacitor, said operational amplifier having a first input terminal connected to an output of said difference circuit and a second input terminal connected to a constant potential, said feedback capacitor being inserted between the first input terminal and an output terminal of said operational amplifier.

4. The image sensor according to claim 3,
    wherein said readout circuit simultaneously outputs the signal generated by said first photodiode and the signal generated by said second photodiode, and
    said difference circuit includes a capacitor having a first terminal connected to said first photodiode and a second terminal connected to said second photodiode.

5. The image sensor according to claim 2,
    wherein said integration circuit includes a transistor and a first capacitor, said transistor being included in a source follower circuit having a constant current load, said first capacitor being inserted between a gate of said transistor and a constant potential, and
    in said integration circuit, the difference signal is input as a gate-to-source voltage of said transistor.

6. The image sensor according to claim 2,
    wherein said integration circuit includes a transistor having a source which is grounded and a capacitor inserted between a gate and a drain of said transistor, and
    in said integration circuit, the difference signal is input as a gate-to-source voltage of said transistor.

7. The image sensor according to claim 5,
    wherein said readout circuit sequentially outputs the signal generated by said first photodiode and the signal generated by said second photodiode, and
    said difference circuit includes a correlated double sampling circuit having a second capacitor which stores a difference signal corresponding to a difference between the signals sequentially outputted by said readout circuit.

8. The image sensor according to claim 7,
    wherein a capacitance value of said second capacitor is larger than a capacitance value of said first capacitor.

9. The image sensor according to claim 7,
    wherein said integration circuit further includes a third capacitor which is connected in parallel with said second capacitor and which is charged at a predetermined voltage.

10. The image sensor according to claim 7,
    wherein a clamp voltage of said correlated double sampling circuit is lower than a threshold voltage of said transistor.

11. The image sensor according to claim 2,
    wherein the pixel signal is generated within a time of accumulating data for one frame image.

12. The image sensor according to claim 1, further comprising:
    a first polarized light filter above said first photodiode; and
    a second polarized light filter above said second photodiode,
    wherein said first polarized light filter and said second polarized light filter each have different polarized light transmission characteristics.

13. The image sensor according to claim 1, further comprising:
    a first wavelength filter above said first photodiode; and
    a second wavelength filter above said second photodiode,
    wherein said first wavelength filter and said second wavelength filter each have different wavelength transmission characteristics.

14. An electromagnetic radiation imaging device, comprising:
    an electromagnetic radiation source which generates electromagnetic radiation;
    a light source which generates probe light;
    a superimposing optical element which superimposes, with the probe light, the electromagnetic radiation that has one of transmitted through and reflected off an object;
    an electro-optical modulator into which the superimposed electromagnetic radiation and probe light enter, and which modulates a specific physical quantity of the probe light according to an electric field of the electromagnetic radiation; and
    the image sensor according to claim 1 which captures the probe light that has been modulated.

15. The electromagnetic radiation imaging device according to claim 14,
    wherein said light source generates pulsed probe light, and said image sensor captures the modulated probe light in synchronization with a pulse of the pulsed probe light.

16. A method for driving the image sensor according to claim 9, comprising:
    supplying a predetermined voltage of said third capacitor to the integration circuit; and
    inputting a difference signal to the integration circuit after supplying the predetermined voltage to the integration circuit.

* * * * *